US009029515B2

(12) United States Patent
Pons et al.

(10) Patent No.: US 9,029,515 B2
(45) Date of Patent: May 12, 2015

(54) ANTI-PCSK9 ANTIBODIES WITH PH DEPENDENT ANTIGEN BINDING

(75) Inventors: Jaume Pons, San Bruno, CA (US); Jeffrey Raymond Chabot, Medford, MA (US); Javier Fernando Chaparro Riggers, San Mateo, CA (US); Bruce Charles Gomes, Ashburnham, MA (US); Hong Liang, San Francisco, CA (US); Kapil Mayawala, Peabody, MA (US); Jerome Thomas Mettetal, II, Cambridge, MA (US); Arvind Rajpal, San Francisco, CA (US); David Louis Shelton, Oakland, CA (US)

(73) Assignees: Rinat Neuroscience Corp., South San Francisco, CA (US); Pfizer Inc., New York, NY (US)

( * ) Notice: Subject to any disclaimer, the term of this patent is extended or adjusted under 35 U.S.C. 154(b) by 551 days.

(21) Appl. No.: 13/045,345

(22) Filed: Mar. 10, 2011

(65) Prior Publication Data

US 2011/0229489 A1 Sep. 22, 2011

Related U.S. Application Data

(60) Provisional application No. 61/313,102, filed on Mar. 11, 2010, provisional application No. 61/447,638, filed on Feb. 28, 2011.

(51) Int. Cl.

| | |
|---|---|
| ***C07K 16/00*** | (2006.01) |
| ***C07K 16/40*** | (2006.01) |
| ***C07K 16/42*** | (2006.01) |

(52) U.S. Cl.

CPC ............. *C07K 16/40* (2013.01); *C07K 16/4291* (2013.01); *C07K 2317/565* (2013.01); *C07K 2317/70* (2013.01); *C07K 2317/76* (2013.01); *C07K 2317/92* (2013.01); *C07K 2317/94* (2013.01); *C07K 2319/21* (2013.01)

(58) Field of Classification Search

None

See application file for complete search history.

(56) References Cited

U.S. PATENT DOCUMENTS

| | | | |
|---|---|---|---|
| 6,326,155 B1 | 12/2001 | Maclennan et al. | |
| 6,946,548 B2 | 9/2005 | Sarkar et al. | |
| 2009/0324589 A1 | 12/2009 | Igawa et al. | |
| 2010/0166768 A1 | 7/2010 | Sleeman et al. | |
| 2010/0239577 A1 | 9/2010 | Igawa et al. | |
| 2011/0076275 A1 | 3/2011 | Igawa et al. | |
| 2011/0111406 A1 | 5/2011 | Igawa et al. | |
| 2011/0245473 A1 | 10/2011 | Igawa et al. | |
| 2013/0085266 A1* | 4/2013 | Sleeman et al. | 530/387.9 |

FOREIGN PATENT DOCUMENTS

| | | |
|---|---|---|
| JP | 2009-069095 | 3/2009 |
| WO | WO 95/14710 A1 | 6/1995 |
| WO | WO 03/080672 A1 | 10/2003 |

OTHER PUBLICATIONS

Almagro, C., et al., "Humanization of antibodies," *Frontiers in Bioscience*, 2008, 1619-1633, vol. 13.

Ewert, S., et al., "Stability improvement of antibodies for extracellular and intracellular applications: CDR grafting to stable frameworks and structure-based framework engineering," *Methods*, 2004, 184-199, vol. 34.

Hinton, P., et al., "An Engineered Human IgG1 Antibody with Longer Serum Half-Life," *The Journal of Immunology*, 2006, 346-356, vol. 176.

Igawa, T., et al., "Antibody recycling by engineered pH-dependent antigen binding improves the duration of antigen neutralization," *Nature Biotechnology*, 2010, 1203-1208, vol. 28, No. 11.

Igawa, T., et al., "Reduced elimination of IgG antibodies by engineering the variable region," *Protein Engineering, Design & Selection*, 2010, 385-392, vol. 23, No. 5.

Ito, W., et al., "The His-probe method: effects of histidine residues introduced into the complementarity-determining regions of antibodies on antigen-antibody interactions at different pH values," *Federation of European Biochemical Societies Letters*,1992, 85-88, vol. 309, No. 1.

Junghans, R., et al., "The protection receptor for IgG catabolism is the $\beta_2$-microglobulin-containing neonatal intestinal transport receptor," *Proceedings of the National Academy of Sciences USA*, 1996, 5512-5516, vol. 93.

Lee, D., et al., "RAP Uses a Histidine Switch to Regulate Its Interaction with LRP in the ER and Golgi," *Molecular Cell*, 2006, 423-430, vol. 22.

Maeda, K., et al., "pH-Dependent Receptor/Ligand Dissociation as a Determining Factor for Intracellular Sorting of Ligands for Epidermal Growth Factor Receptors in Rat Hepatocytes," *Journal of Controlled Release*, 2002, 71-82, vol. 82, No. 1.

(Continued)

*Primary Examiner* — Sharon Wen

(74) *Attorney, Agent, or Firm* — Pfizer Inc.

(57) ABSTRACT

The present invention relates to antibodies with pH dependent binding to its antigen such that the affinity for antigen binding at physiological pH (i.e., pH 7.4) is greater than at endosomal pH (i.e., pH 6.0 or 5.5). In other words, the $K_D$ or $k_{off}$ ratio at pH 5.5/pH 7.4 or at pH 6.0/pH 7.4 is more than, or ranges between, 2, 3, 4, 8, 10, 16, 20, 30, 40, or 100 or more. Such pH dependent antibodies preferentially dissociate from the antigen in the endosome. This can increase antibody half life, as compared to antibodies with equivalent $K_D$s at pH 7.4 but with no pH dependent binding, when the antigen is one that undergoes antigen-mediated clearance (e.g., PCSK9). Antibodies with pH dependent binding can decrease total antigen half life when the antigen undergoes reduced clearance when bound to antibody (e.g., IL6). Antibodies with pH dependent binding can also prolong the decrease in antigen which is not antibody-bound. This can be important when antagonizing a target antigen typically present at high levels (e.g., IgE, DKK1, C5 and SOST). In addition, such antibodies can increase antigen half life when the antigen is a receptor and the receptor has increased clearance when bound to antibody (e.g., GMCSF receptor).

4 Claims, 16 Drawing Sheets

(56) References Cited

OTHER PUBLICATIONS

Martin, W., et al., "Crystal Structure at 2.8 Å of an FcRn/Heterodimeric Fc Complex: Mechanism of pH-Dependent Binding," *Molecular Cell*, 2001, 867-877, vol. 7.
Maxfield, F., et al., "Endocytic Recycling," *Nature Reviews Molecular Cell Biology*, 2004, 121-132, vol. 5, No. 2.
Pavlinkova, G., et al., "Charge-Modified Single Chain Antibody Constructs of Monoclonal Antibody CC49: Generation, Characterization, Pharmacokinetics, and Biodistribution Analysis," *Nuclear Medicine and Biology*, 1999, 27-34, vol. 26.
Presta, L.G., "Molecular engineering and design of therapeutic antibodies," *Current Opinion in Immunology*, 2008, 460-470, vol. 20.
Raghavan, M., et al., "Analysis of the pH Dependence of the Neonatal Fc Receptor/Immunoglobulin G Interaction Using Antibody and Receptor Variants," *Biochemistry*, 1995, 14649-14657, vol. 34.
Sarkar, C., et al., "Rational cytokine design for increased lifetime and enhanced potency using pH-activated "histidine switching"," *Nature Biotechnology*, 2002, 908-913, vol. 20.
Tamura, M., et al., "Structural Correlates of an Anticarcinoma Antibody: Identification of Specificity-Determining Residues (SDRs) and Development of a Minimally Immunogenic Antibody Variant by Retention of SDRs Only," *The Journal of Immunology*, 2000, 1432-1441. vol. 164.
Tan, P., et al., ""Superhumanized" Antibodies: Reduction of Immunogenic Potential by Complementarity-Determining Region Grafting with Human Germline Sequences: Application to an Anti-CD28," *The Journal of Immunology*, 2002, 1119-1125, vol. 169.
Watanabe, H., et al., "Optimizing pH Response of Affinity between Protein G and IgG Fc," *The Journal of Biological Chemistry*, 2009, 12373-12383, vol. 284, No. 18.
Zalevsky, J., et al., "Enhanced antibody half-life improves in vivo activity," *Nature Biotechnology*, 2010, 157-159, vol. 28, No. 2.

* cited by examiner

* one outlier in 5A10 group eliminated

** mAb concentrations below detection limit are replaced with the detection limit value IGE
Normal Antibody (R=1)
Acid Switched Antibody (R depends on col.)
R=k_off @ pH 6)/(k_off @ pH 7.4)
K_D=0.1nM
K_D=1.0nM
K_D=10nM
K_D=100M
R=3
R=10
R=30
Free Ligand [M]
Time [days]
10-8
10-10
10-12
0
50
100

C5
Normal Antibody (R=1)
Acid Switched Antibody (R depends on col.)
R=koff @ pH 6)/(koff @ pH 7.4)
KD=0.1nM
KD=1.0nM
KD=10nM
KD=100M
R=3
R=10
R=30
Free Ligand [M]
Time [days]
0
50
100
10-6
10-7
10-8
10-10

ANTI-PCSK9 ANTIBODIES WITH PH DEPENDENT ANTIGEN BINDING

This application claims priority, under 35 USC §119(e), to U.S. Provisional Application Ser. No. 61/313,102, filed Mar. 11, 2010, and U.S. Provisional Application Ser. No. 61/447,638, filed Feb. 28, 2011, hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "SequenceListingPC33956A.txt" created on Mar. 7, 2011 and having a size of 12 KB. The sequence listing contained in this .txt file is part of the specification and is herein incorporated by reference in its entirety.

FIELD OF THE INVENTION

The present invention relates to antibodies, e.g., full length antibodies or antigen-binding portions thereof, that have pH dependent binding such that the $K_D$ and/or $k_{off}$ ratio at endosomal pH/physiologic pH (e.g., pH 5.5/pH 7.4 or pH 6.0/pH 7.4) is 2 or greater.

BACKGROUND OF THE INVENTION

Monoclonal antibodies (mAbs) have become important therapeutic options for numerous diseases (Brekke and Sandlie, Nat Rev Drug Discov 2: 52-62, 2003; Maggon, Curr Med Chem 14: 1978-1987, 2007). Most of the mAbs now on the market are IgG antibodies. Their relatively long half-life is mediated by FcRn binding. IgG uptake into the cell occurs via fluid phase pinocytosis, and the IgG subsequently binds to FcRn in the acidified environment (pH 6.0) of the endosomal compartment (Lobo et al., J Pharm Sci 93: 2645-2668, 2004). FcRn-bound IgG is thought to be protected from degradation by recycling to the cell surface where the neutral pH facilitates dissociation and release of the IgG into circulation. Unbound IgG, by contrast, is believed to be transferred to lysosomes and subsequently degraded (Lencer and Blumberg, Trends Cell Biol 15: 15: 5-9, 2005).

Recently, various technologies for optimizing the functional activity of an IgG antibody by introducing specific substitutions have been applied in order to reduce dose and/or dose frequency and improve efficacy and safety (Presta, Curr. Opinion Immunol 20: 460-470, 2008). Generally, optimization of IgG antibodies can be classified into engineering the Fc constant region, to impact antibody binding to FcRn, FcγR and the complement system, and engineering the variable region to impact binding affinity.

Several works describe engineering the constant region to increase binding to Fc γ-receptors and thus enhance the effector function of an IgG1 antibody (Stavenhagen et al., Cancer Res 67: 8882-8890, 2007; Zalevsky et al., Blood 113: 3735-3743, 2009). Substitutions such as S239D/I332E/A330L or F243L/R292P/Y300L/V3051/P396L into IgG1 have been shown to improve Fc γ-receptor IIIa binding and exhibit superior antibody-dependent cellular cytotoxicity (ADCC) activity in vitro and superior efficacy in vivo compared with wild-type IgG1. Hence, compared with wild-type antibodies, antibodies with such substitutions are expected to show superior efficacy at the same dose or comparable efficacy at a lower dose and/or with lesser frequency of dosing in human.

Another method to lower the dose and/or frequency of dosing is to reduce the elimination of an IgG antibody. The long half-life of IgG antibodies is reported to be dependent on its binding to FcRn. Therefore, substitutions that increase the binding affinity of IgG to FcRn at pH 6.0 while maintaining the pH dependence of the interaction by engineering the constant region have been extensively studied (Ghetie et al., Nature Biotech. 15: 637-640, 1997; Hinton et al., JBC 279: 6213-6216, 2004; Dall'Acqua et al., J Immunol 117: 1129-1138, 2006). Substitutions, such as M428L/N434S, led to increased half life and an increased pharmacodynamic effect in the variants (Zalevsky et al., Nature Biotech. 28: 157-159, 2010). Several works have reported successful increase in the half-life by introducing substitutions such as T250Q/M428L or M252Y/S254T/T256E to increase binding to FcRn at an acidic pH. In a non-human primate pharmacokinetic study, T250Q/M428L substitution to IgG1 showed a half-life of 35 days, a significant increase over the 14-day half-life of wild-type IgG1 (Hinton et al., J Immunol 176: 346-356, 2006).

Although substitutions in the constant region are able to significantly improve the functions of therapeutic IgG antibodies, substitutions in the strictly conserved constant region have the risk of immunogenicity in human (Presta, supra, 2008; De Groot and Martin, Clin Immunol 131: 189-201, 2009) and substitution in the highly diverse variable region sequence might be less immunogenic. Reports concerned with the variable region include engineering the CDR residues to improve binding affinity to the antigen (Rothe et al., Expert Opin Biol Ther 6: 177-187, 2006; Bostrom et al., Methods Mol Biol 525: 353-376, 2009; Thie et al., Methods Mol Biol 525: 309-322, 2009) and engineering the CDR and framework residues to improve stability (Wön and Plückthun, J Mol Biol 305: 989-1010, 2001; Ewert et al., Methods 34: 184-199, 2004) and decrease immunogenicity risk (De Groot and Martin, supra, 2009; Jones et al., Methods Mol Bio 525: 405-423, xiv, 2009). As reported, improved affinity to the antigen can be achieved by affinity maturation using the phage or ribosome display of a randomized library. Improved stability can be rationally obtained from sequence- and structure-based rational design. Decreased immunogenicity risk (deimmunization) can be accomplished by various humanization methodologies and the removal of T-cell epitopes, which can be predicted using in silico technologies or determined by in vitro assays. Additionally, variable regions have been engineered to lower pl. A longer half life was observed for these antibodies as compared to wild type antibodies despite comparable FcRn binding (Igawa et al., PEDS, Advance Access, doi: 10.1093/protein/gzq009, 2010).

The present invention relates to engineering or selecting antibodies with pH dependent antigen binding to modify antibody and/or antigen half life. IgG2 antibody half life can be shortened if antigen-mediated clearance mechanisms normally degrade the antibody when bound to the antigen. Similarly, the antigen:antibody complex can impact the half-life of the antigen, either extending half-life by protecting the antigen from the typical degradation processes, or shortening the half-life via antibody-mediated degradation. The present invention relates to antibodies with higher affinity for antigen at pH 7.4 as compared to endosomal pH (i.e., pH 5.5-6.0) such that the $K_D$ ratio at pH 5.5/pH 7.4 or at pH 6.0/pH 7.4 is 2 or more.

The invention relates to an antibody with such pH dependent binding to its antigen, and methods of designing, making and using such antibodies. Examples of useful antibodies target antigens such as proprotein convertase subtilisin kexin type 9 (PCSK9), also known as NARC-1, IgE, dickkopfrelated protein 1 (DKK1), Complement 5 (C5), sclerostin (SOST) and GMCSF receptor.

PCSK9 was identified as a protein with a genetic mutation in some forms of familial hypercholesterolemia. PCSK9 is synthesized as a zymogen that undergoes autocatalytic processing at a particular motif in the endoplasmic reticulum. Population studies have shown that some PCSK9 mutations are "gain-of-function" and are found in individuals with autosomal dominant hypercholesterolemia, while other "loss-of-function" (LOF) mutations are linked with reduced plasma cholesterol. Morbidity and mortality studies in this group clearly demonstrated that reducing PCSK9 function significantly diminished the risk of cardiovascular disease.

SUMMARY OF THE INVENTION

The present invention relates to antibodies with pH dependent binding to its antigen such that the affinity for antigen binding at physiological pH (i.e., pH 7.4) is greater than at endosomal pH (i.e., pH 6.0 or 5.5). In other words, the $K_D$ or $k_{off}$ ratio at pH 5.5/pH 7.4 or at pH 6.0/pH 7.4 is more than, or ranges between, 2, 3, 4, 8, 10, 16, 20, 30, 40, or 100 or more. Such pH dependent antibodies preferentially dissociate from the antigen in the endosome. This can increase antibody half life, as compared to antibodies with equivalent $K_D$s at pH 7.4 but with no pH dependent binding, when the antigen is one that undergoes antigen-mediated clearance (e.g., PCSK9). Antibodies with pH dependent binding can decrease total antigen half life when the antigen undergoes reduced clearance when bound to antibody (e.g., IL6). Antibodies with pH dependent binding can also prolong the antibody-mediated decrease in antigen which is not antibody-bound. This can be important when antagonizing a target antigen typically present at high levels (e.g., IgE, DKK1, C5 and SOST). In addition, such antibodies can increase antigen half life when the antigen is a receptor and the receptor has increased clearance when bound to antibody (e.g, GMCSF receptor). In any embodiment of the invention described below, the $K_D$ and $k_{off}$ can be measured at either 25° C. or 37° C.

In a preferred embodiment, the antibody with pH dependent binding which specifically binds an antigen with higher affinity at pH 7.4 than at pH 6.0, wherein the $K_D$ ratio and/or the $k_{off}$ ratio at pH 6.0/pH 7.4 and at 25° C. is more than, or ranges between, 2, 3, 4, 8, 10, 16, or more, and wherein the antibody has reduced plasma clearance in vivo when exposed to said antigen as compared to an antibody without pH dependent binding that has a similar affinity for the antigen at pH 7.4, but has a comparable $K_D$ and/or $k_{off}$ ratio at pH 6.0/pH 7.4 that is less than 2. Preferably, the antigen is not interleukin-6 receptor (IL6R), or, preferably, the antibody is not an anti-IL6R antibody Fv3-m73, Fv-4-m73 or H3pl/L73 as disclosed in WO 2010/106812 or WO 2009/041621.

In another preferred embodiment, the antibody with pH dependent binding which specifically binds an antigen with higher affinity at pH 7.4 than at pH 6.0, wherein the $K_D$ ratio and/or the $k_{off}$ ratio at pH 6.0/pH 7.4 and at 25° C. is more than, or ranges between, 2, 3, 4, 8, 10, 16, or more, and wherein the antigen is both membrane bound and soluble in vivo and wherein the antibody mediates increased localization to a cell membrane receptor as compared to an antibody that has a similar affinity for the antigen at pH 7.4 but has a comparable $K_D$ and/or $k_{off}$ ratio at pH 6.0/pH 7.4 that is less than 2. Preferably, the antigen is not the IL6R or, preferably, the antibody is not an anti-IL6R antibody Fv3-m73, Fv-4-m73 or H3pl/L73 as disclosed in WO 2010/106812 or WO 2009/041621. In another preferred embodiment, the antigen is a soluble receptor that is a non-signaling decoy. In still other preferred embodiments, the antibody with pH dependent binding is an antibody drug conjugate, mediates antibody dependent cell-mediated cytotoxicity (ADCC), and/or complement-dependent cytotoxicity (CDC).

The invention includes an antibody with pH dependent binding which specifically binds an antigen with higher affinity at pH 7.4 than at pH 6.0, wherein the $K_D$ ratio and/or the $k_{off}$ ratio at pH 6.0/pH 7.4 and at 25° C. is more than, or ranges between, 2, 3, 4, 8, 10, 16, or more, and wherein the decrease in the in vivo amount of non-antibody bound antigen is prolonged when exposed to said antibody as compared to an antibody without pH dependent binding that has a similar affinity for the antigen at pH 7.4, but has a comparable $K_D$ and/or $k_{off}$ ratio at pH 6.0/pH 7.4 that is less than 2.

The invention provides an antibody with pH dependent binding which specifically binds an antigen with higher affinity at pH 7.4 than at pH 6.0, wherein the $K_D$ ratio and/or the $k_{off}$ ratio at pH 6.0/pH 7.4 and at 25° C. is more than, or ranges between, 2, 3, 4, 8, 10, 16, or more, and wherein there is a decrease in the vivo amount of antibody-bound antigen as compared to an antibody without pH dependent binding that has a similar affinity for the antigen at pH 7.4, but has a comparable $K_D$ and/or $k_{off}$ ratio at pH 6.0/pH 7.4 that is less than 2. In a preferred embodiment, the antigen is osteopontin.

The invention also provides for an agonist antibody with pH dependent binding which specifically binds an antigen with higher affinity at pH 7.4 than at pH 6.0, wherein the $K_D$ ratio and/or the $k_{off}$ ratio at pH 6.0/pH 7.4 and at 25° C. is more than, or ranges between, 2, 3, 4, 8, 10, 16, or more, and wherein the antigen is a receptor and the receptor has reduced clearance in vivo when exposed to said antibody as compared to an antibody that has similar affinity for the receptor at pH 7.4, but has a comparable $K_D$ and/or $k_{off}$ ratio at pH 6.0/pH 7.4 that is less than 2. In a preferred embodiment, the receptor is GMCSF receptor.

In other preferred embodiments of any of the preceding antibodies, the $K_D$ ratio or $k_{off}$ ratio at pH 6.0/pH 7.4 is more than, or ranges between, 20, 30, 40 or 100 or more. In other preferred embodiments, the preferred $K_D$ ratio or $k_{off}$ ratio at pH 6.0/pH 7.4 ranges between 2-3, 2-4, 2-8, 2-10, 2-16, or 2-20 or more, or 3-4, 3-8, 3-10, 3-16 or 3-20, or 4-8, 4-10, 4-16, or 4-20 or more, or 8 to 10, 8-16, 8-20 or more, 10-16, 10-20 or more, or 16-20 or more.

In other preferred embodiments of the previously described antibodies, the antibody binding to the antigen at pH 7.4 and at pH 25° C. has a $K_D$ of about 0.01 nM to about 100 nM, or, more preferably, at about 0.1 nM to about 10 nM.

In other preferred embodiments of the previously described antibodies, the binding of the antibody to the antigen at pH 7.4 has a $k_{off}$ of about 1×10E-4 s-1 to about 1×10E-1 s-1, more preferably, about 1×10E-3 s-1 to about 1×10E-1 s-1.

In another preferred embodiment of the previously described antibodies, the antigen is PCSK9. In one preferred embodiment, the anti-PCSK9 antibody is not PCSK9 antibody H1M300N (see US2010/0166768). In other preferred embodiments, the antigen is IgE, C5, or DKK1 and, in preferred embodiments, the $K_D$ ranges between 1.0 nM to about 10 nM or between 1.0 nM to about 100 nM.

The invention also provides a method of extending interval dosing and/or decreasing the therapeutic dose for treating a patient with a therapeutic antibody, said method comprising administering to the patient a therapeutically effective amount of the antibody of any of the previously described antibodies of the invention, wherein said antibody has an extended pharmacodynamic effect and/or half life as compared to an antibody that has similar affinity at pH 7.4, but has a $K_D$ ratio and/or $k_{off}$ ratio at pH 6.0/7.4 and at 25° C. that is less than 2.

Also contemplated by the invention is a method of making an antibody with prolonged half-life and/or pharmacodynamic effect by regulating antibody binding affinity in a pH dependent manner, said method comprising selecting for antibody CDR histidine residues or other residues that optimize the microenvironment affecting pKa, such that antibody antigen binding has a $K_D$ ratio and/or $k_{off}$ ratio at pH 6.0/pH7.4 that is more than, or ranges between, 2, 3, 4, 8, 10, 16, or more. The invention also contemplates antibodies made by this method, including antibodies with 1, 2, 3, 4, 5, or more histidine substitutions in CDR residues that optimize the microenvironment affecting pKa.

In a preferred embodiment of the above-described method, the method further comprises mutagenizing the antibody to achieve antibody affinity with a $K_D$ at pH 7.4 of at least 100 nM as measured at 25° C. In another embodiment, the invention provides for an antibody library enriched for histidines in CDR residues or other residues that optimize the microenvironment affecting pKa.

In other preferred embodiments, the invention provides an isolated antibody which specifically binds to PCSK9 and comprises a heavy chain variable region (VH) complementary determining region one (CDR1), a VH CDR2, and a VH CDR3 from the VH amino acid sequence shown in SEQ ID NO: 4 or 5 or a variant thereof having one, two, three or more conservative amino acid substitutions in CDR1, CDR2, and/or CDR3.

In a preferred embodiment, the antibody further comprises the light chain variable region (VL) CDR1, CDR2, and CDR3 of the VL amino acid sequence shown in SEQ ID NO: 3 or a variant thereof having one, two, three or more conservative amino acid substitutions in CDR1, CDR2, and/or CDR3.

The invention also provides for isolated antibody which specifically binds to PCSK9 and comprises a heavy chain variable region (VH) complementary determining region one (CDR1) having the amino acid sequence shown in SEQ ID NO:6, a VH CDR2 having the amino acid sequence shown in SEQ ID NO:7, and/or VH CDR3 having the amino acid sequence shown in SEQ ID NO:8, or a variant thereof having one or more conservative amino acid substitutions in CDR1, CDR2, and/or CDR3, as well as an isolated antibody which specifically binds PCSK9 and comprises a VH CDR1 having the amino acid sequence shown in SEQ ID NO:6, a VH CDR2 having the amino acid sequence shown in SEQ ID NO:7, and/or VH CDR3 having the amino acid sequence shown in SEQ ID NO:9, or a variant thereof having one, two, three or more conservative amino acid substitutions in CDR1, CDR2, and/or CDR3.

In a further embodiment, the invention contemplates an isolated antibody comprising a light chain variable region (VL) CDR1 having the amino acid sequence shown in SEQ ID NO:10, a VL CDR2 having the amino acid sequence shown in SEQ ID NO:11, and/or VL CDR3 having the amino acid sequence shown in SEQ ID NO:12, or a variant thereof having one, two, three or more conservative amino acid substitutions in CDR1, CDR2, and/or CDR3.

In preferred embodiments of the above, the antibody further comprises a VL CDR1 having the amino acid sequence shown in SEQ ID NO:10, a VL CDR2 having the amino acid sequence shown in SEQ ID NO:11, and/or VL CDR3 having the amino acid sequence shown in SEQ ID NO:12, or a variant thereof having one, two, three or more conservative amino acid substitutions in CDR1, CDR2, and/or CDR3, preferably, the VH region comprises SEQ ID NO: 4 or SEQ ID NO: 5 and the VL region comprises SEQ ID NO: 3, or a variant thereof having one, two, three or more conservative amino acid substitutions in SEQ ID NO: 4, SEQ ID NO: 5 and/or SEQ ID NO: 3.

In another preferred embodiment of the PCSK9 antibodies of the present invention, the antibody has one or more Fc mutations, preferably, N434S, N434H, M428L-N434H double mutant, M428L-N434A double mutant, T250Q-M428L double mutant, and M428L-N4345 double mutant In another embodiment, the invention provides for an antibody or antigen-binding portion thereof, encoded by the plasmids deposited at the ATCC and having ATCC Accession No. PTA-10547, or PTA-10548, and/or PTA-10549.

Also contemplated by the invention are pharmaceutical compositions comprising a therapeutically effective amount of any of the above described antibodies, a host cell that recombinantly produces the antibody of any of the previously described antibodies, an isolated nucleic acid encoding any of the previously described antibodies, and an isolated nucleic acid encoding any of the previously described antibodies.

Also contemplated by the invention is a method for reducing a level of LDL-cholesterol in blood of a subject in need thereof, comprising administering to the subject a therapeutically effective amount of any of the antibodies of the invention targeting the PCSK9 antigen.

BRIEF DESCRIPTION OF THE FIGURES/DRAWINGS

Figure 4A:
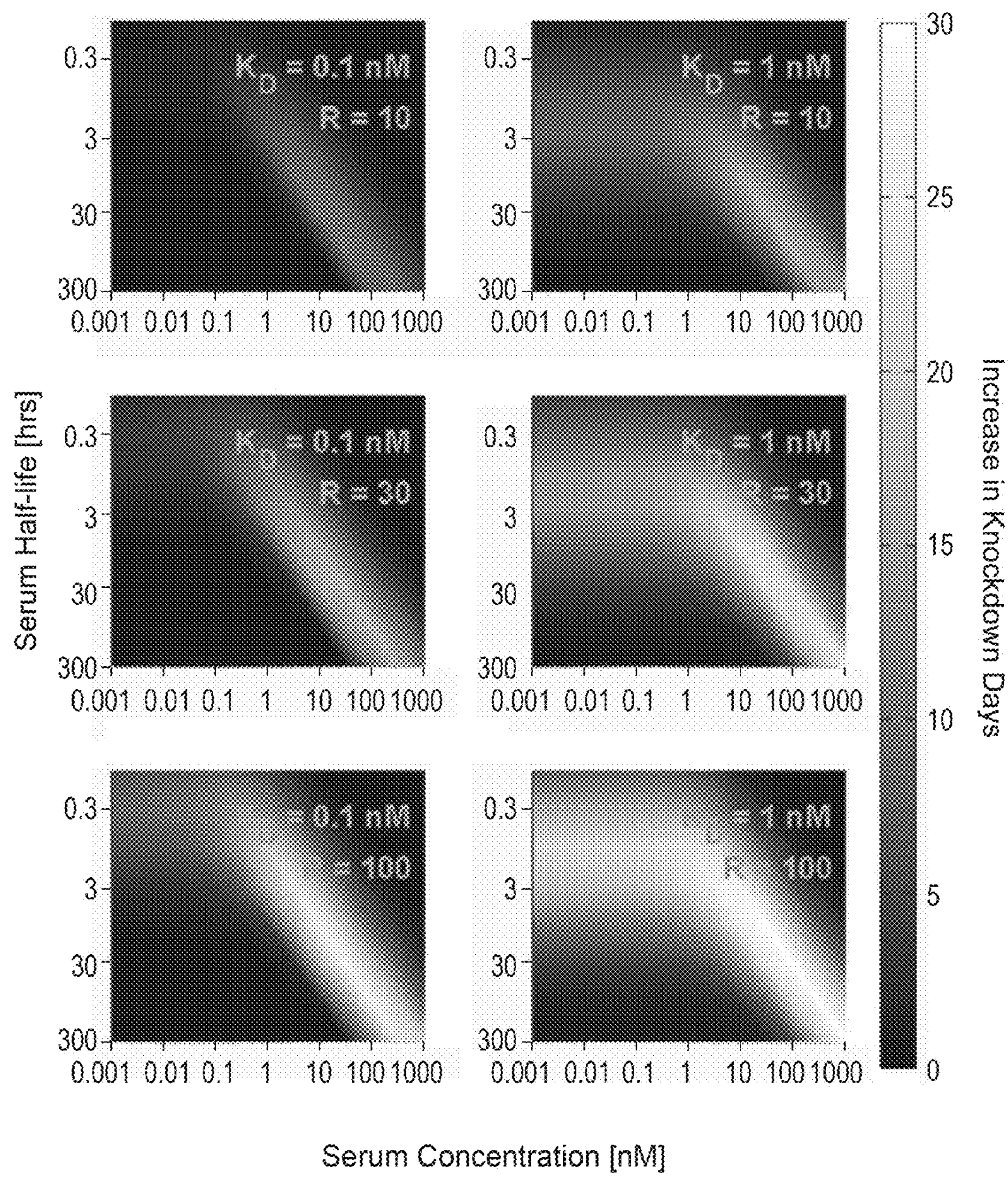
Figure 4B:
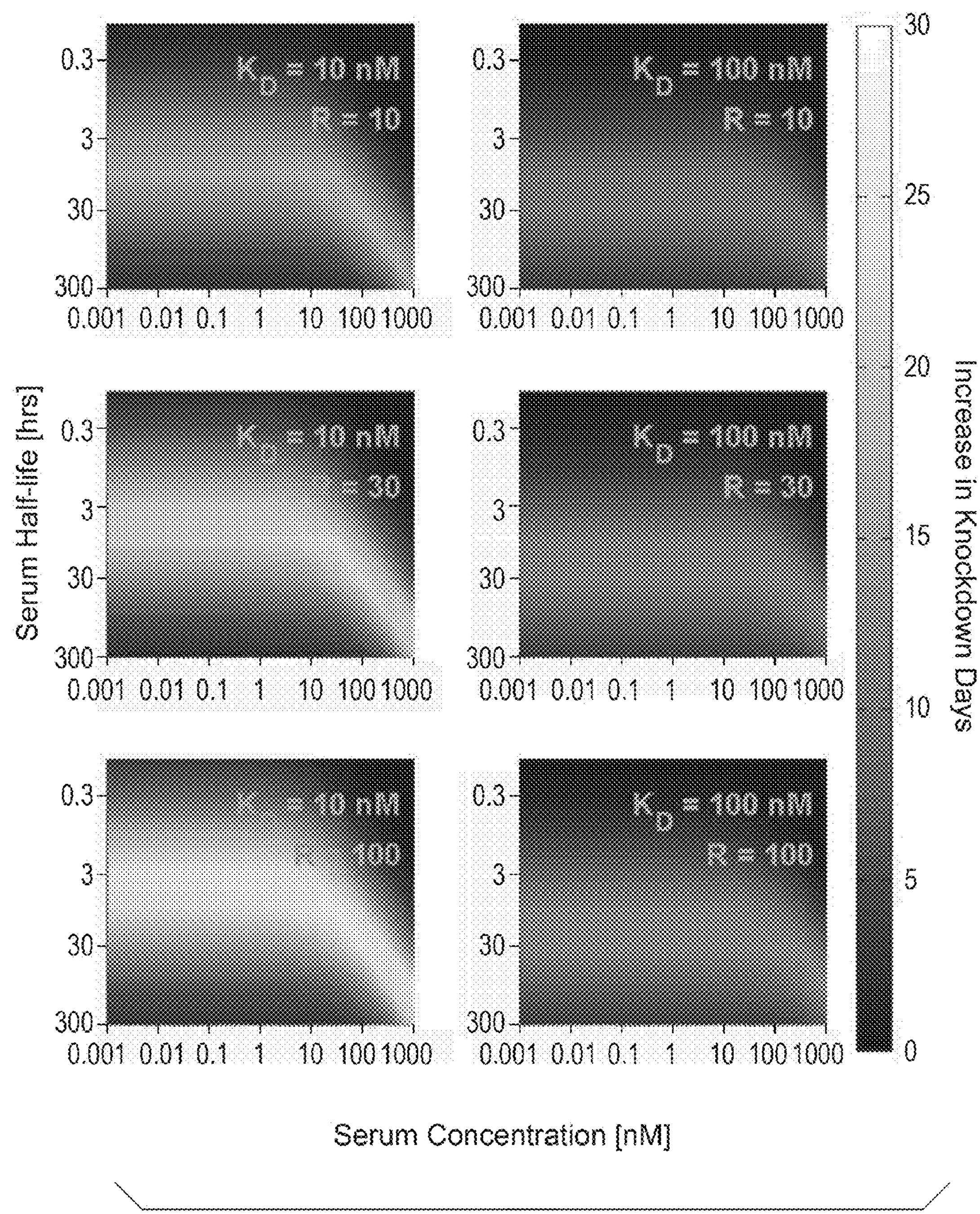

FIG. 4 is a heatmap display showing how many days longer an antibody with pH dependent binding would decrease serum antigen concentration as a function of $K_D$ (R), serum half-life of antigen and serum concentration of antigen. R is equivalent to the $K_D$ ratio at endosomal pH versus physiologic pH. FIG. 4A shows the heatmaps for $K_D$ at 0.1 nM and 1 nM. FIG. 4B shows the heatmaps for $K_D$ at 10 nM and 100 nM.

Figure 5A:
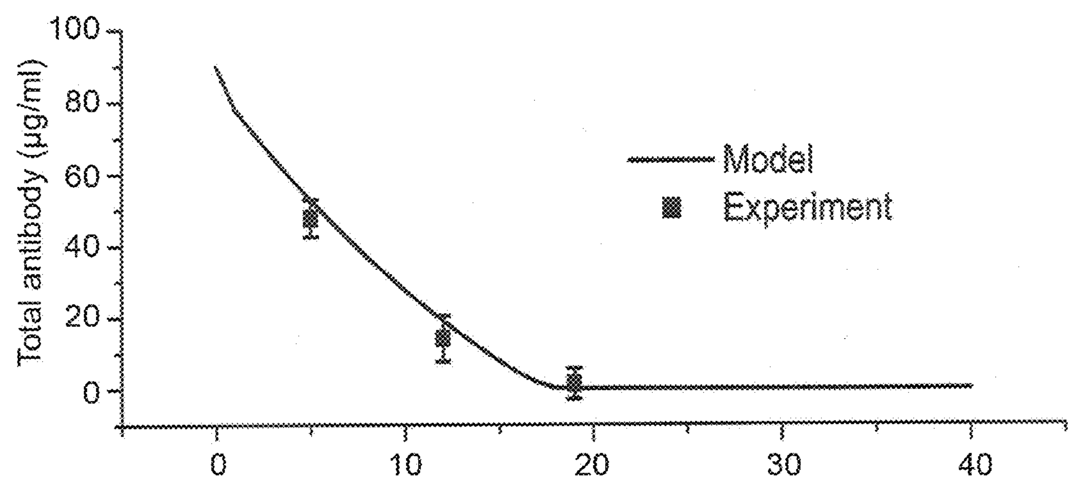
Figure 5B:
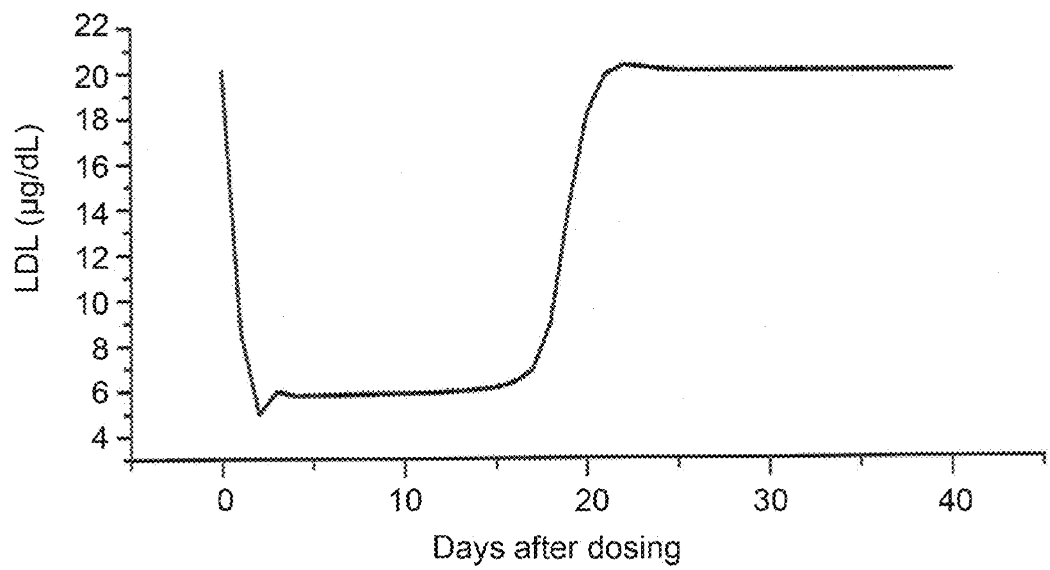

FIG. 5 validates the predictability of the pH dependent antibody modeling. The model successfully predicted the total antibody concentration for 5A10 (FIG. 5A). FIG. 5B is a graph demonstrating the time course effect of 5A10 on LDL.

Figure 6A:
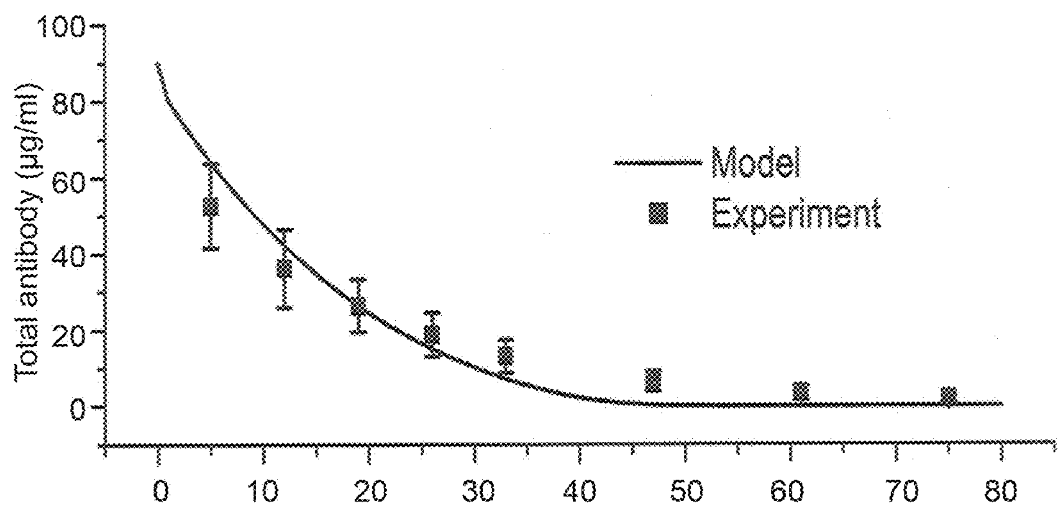
Figure 6B:
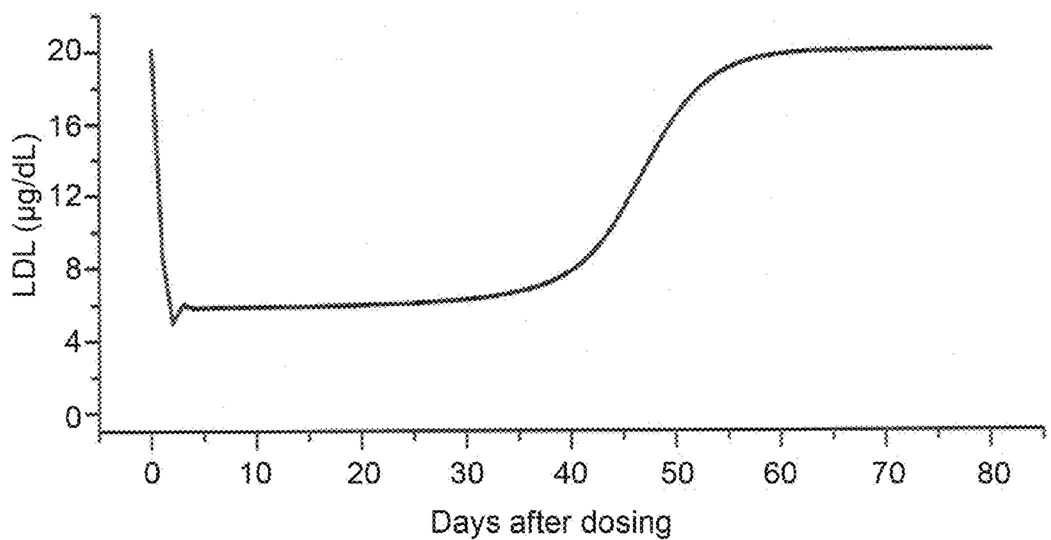

FIG. 6 also validates the predictability of the pH dependent antibody modeling. The model successfully predicted the total antibody concentration for 5L1721H23_6L3H3 (6L3H3) (FIG. 6A). FIG. 6B is a graph demonstrating the time course effect of 6L3H3 on LDL. The pH dependent binding antibody 6L3H3 extended the interval in which LDL was lowered as compared to 5A10.

Figure 7A:
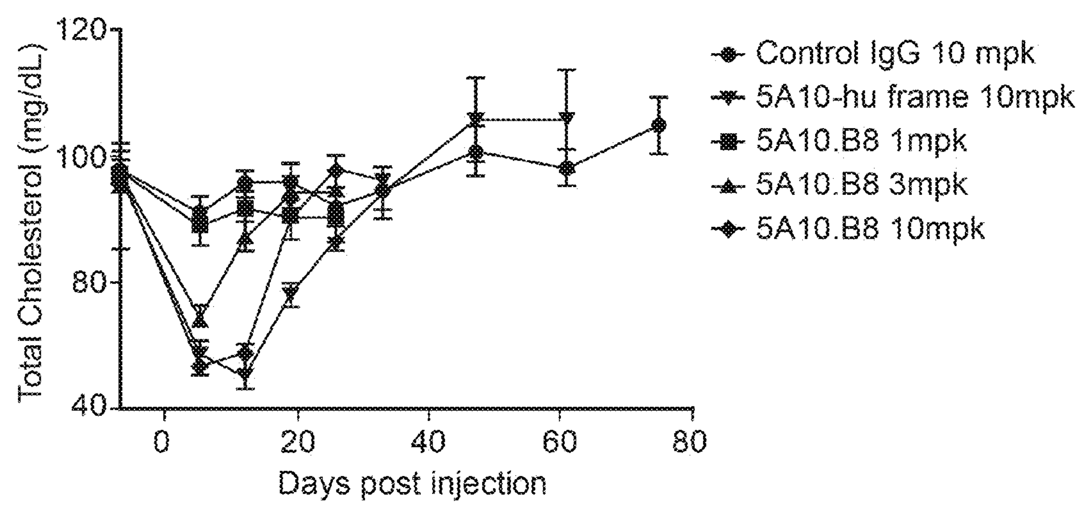
Figure 7B:
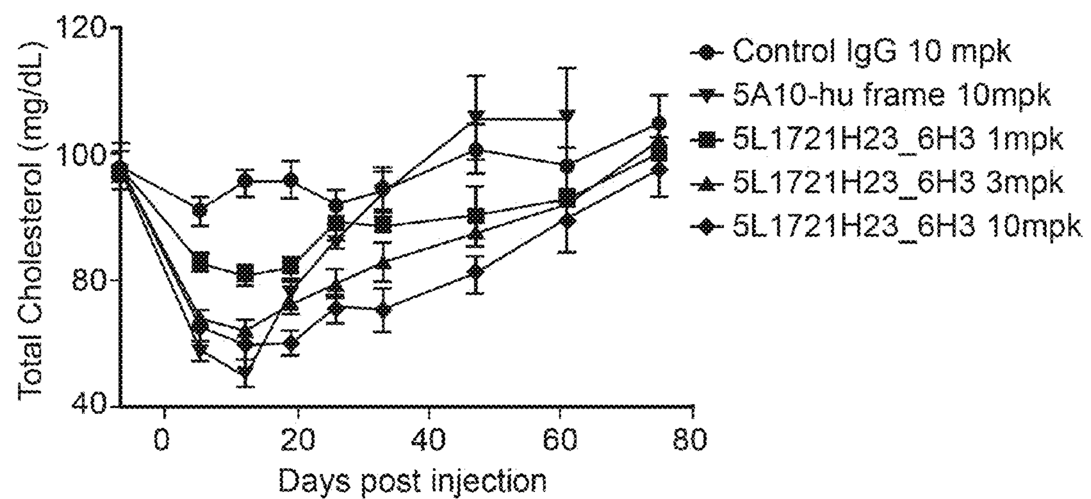

FIG. 7 shows the time course of the total cholesterol effect when administering various PCSK9 antibodies. FIG. 7A shows the dose dependent effect of 5A10 on total cholesterol. FIG. 7B shows the dose dependent effect of pH dependent antibody 5L1721H23_6H3. This effect is extended as compared to the effect of 5A10.

Figure 8A:
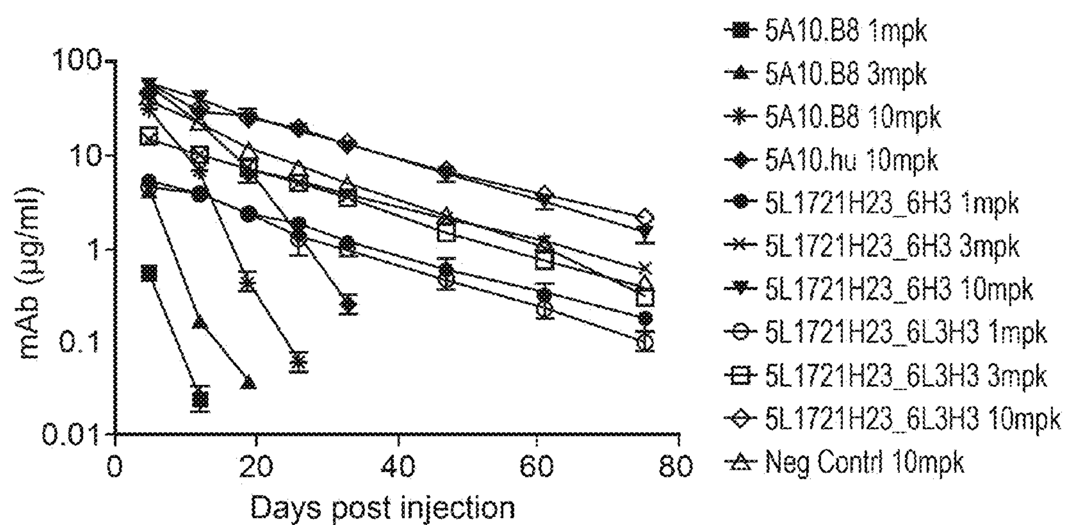
Figure 8B:
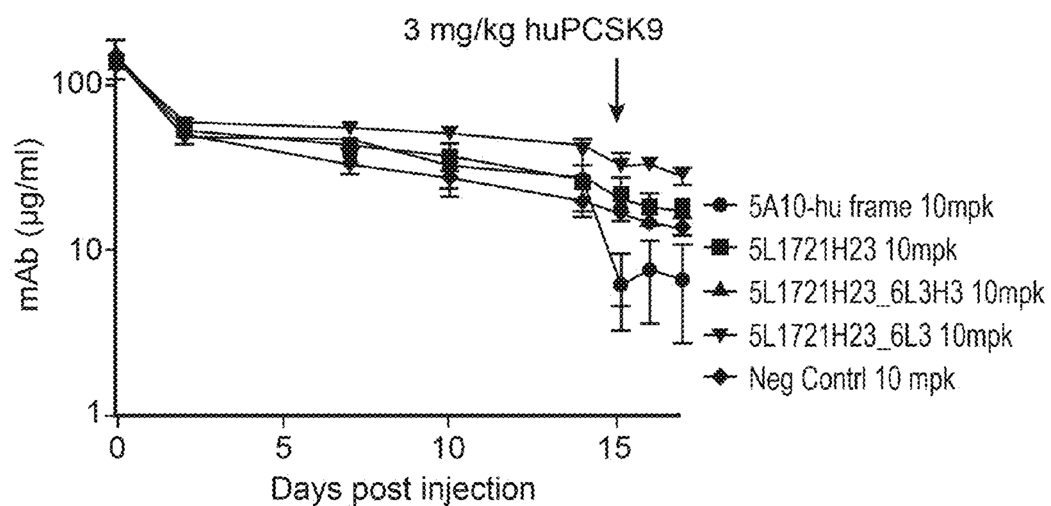

FIG. 8 is a graph which shows that antibodies with pH dependent binding, 5L1721H23_6H3 and 5L1721H23_6L3H3, have reduced antibody degradation and an extended half life as compared to antibodies without pH dependent binding. FIG. 8B is a graph which demonstrates that the effect shown in FIG. 8A is due to target mediated degradation.

Degradation of antibody in PCSK9 null mice increased dramatically following injection of PCSK9.

Figure 9A:
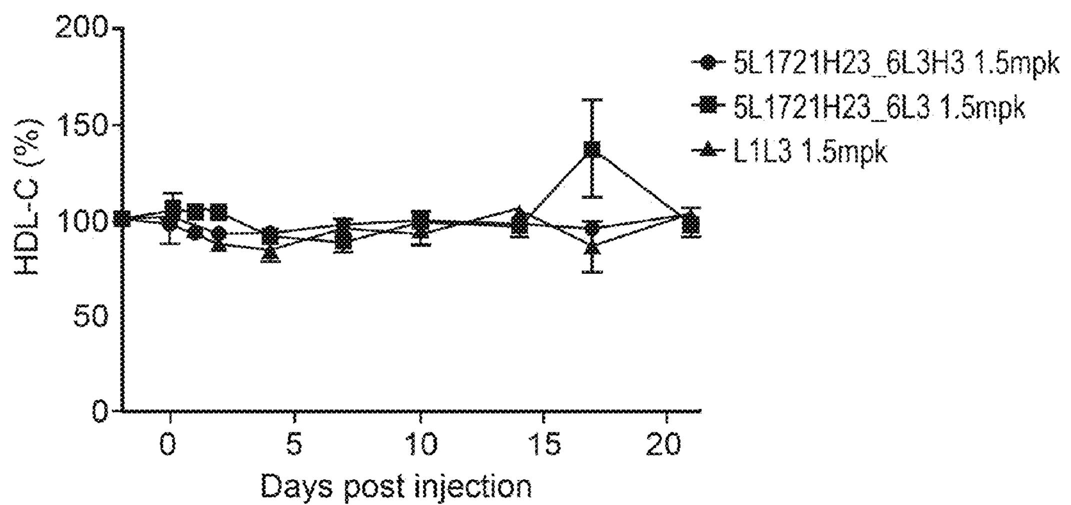
Figure 9B:
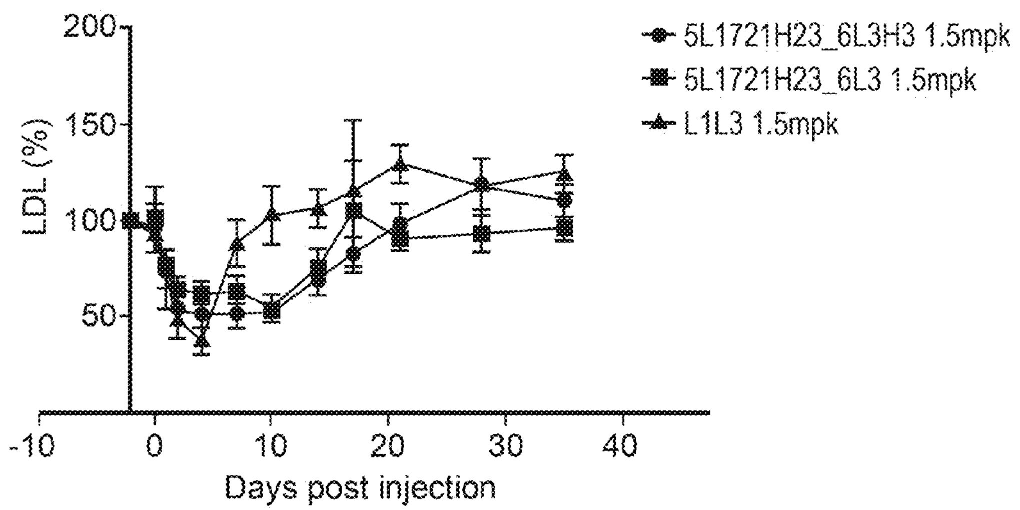

FIG. 9 is a graph which illustrates the effect of pH sensitive PCSK9 antagonist antibodies and non-pH sensitive PCSK9 antagonist antibodies on cholesterol levels in monkeys. While no dramatic change in HDL levels were detected (FIG. 9A), the pH sensitive antibodies mediated a more prolonged reduction in LDL levels (FIG. 9B) as compared to non-pH dependent antibody L1 L3.

Figure 10:
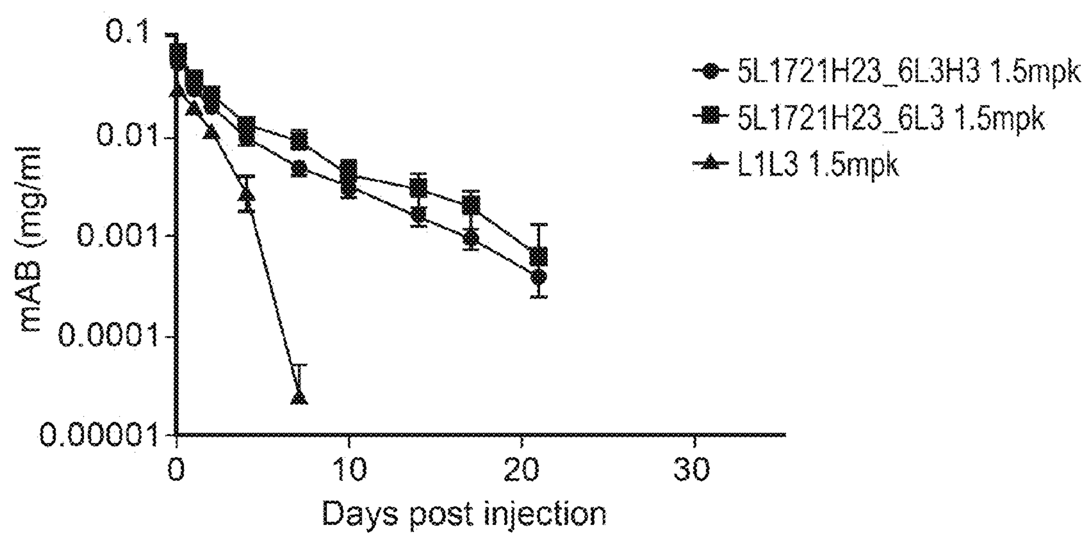

FIG. 10 is a graph demonstrating that the PCSK9 antibodies with pH dependent binding had a prolonged half life in vivo as compared to the non-pH dependent antibodies.

Figure 11:
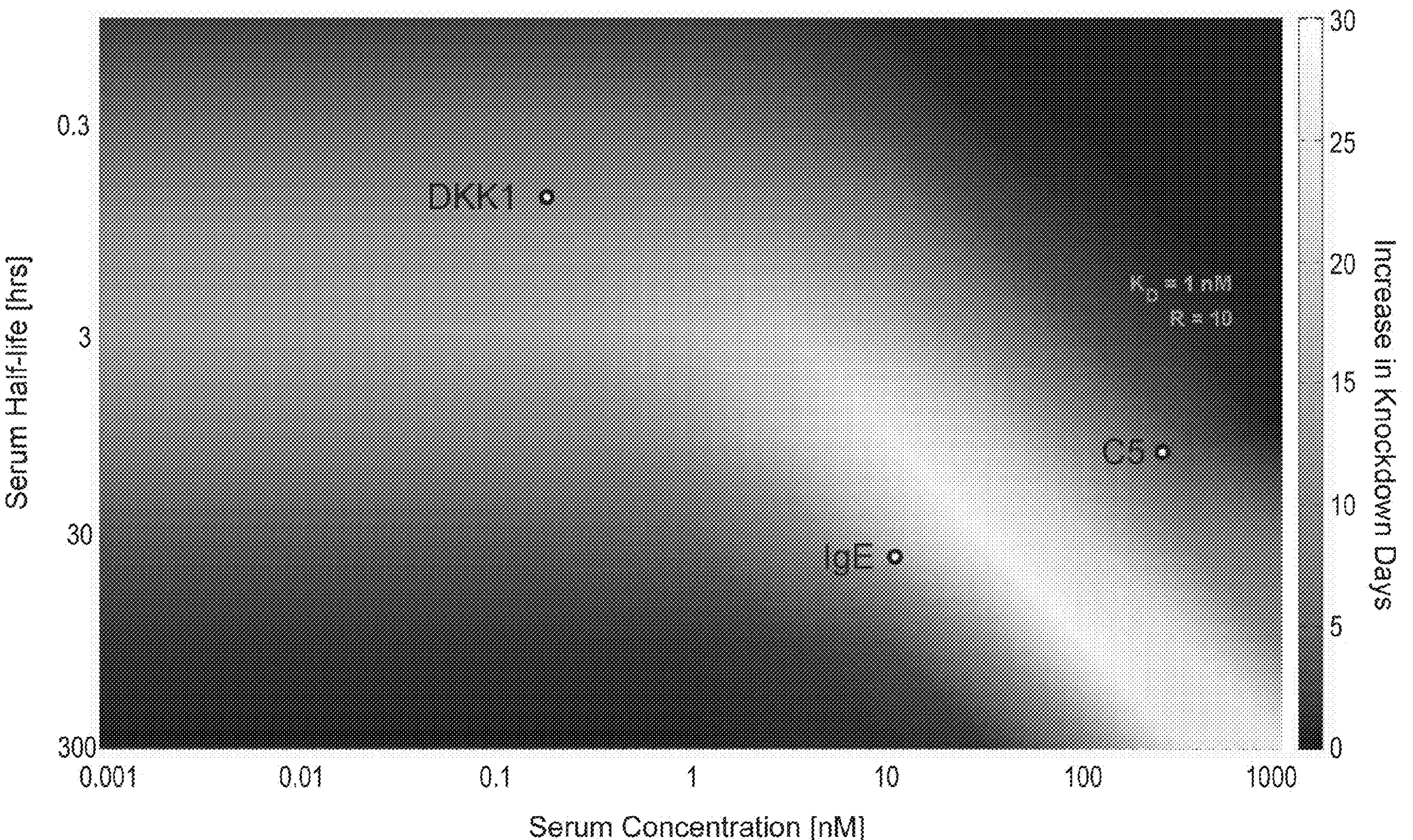

FIG. 11 is a heatmap showing the general modeling for pH dependent binding. Such antibodies directed against antigens DKK1, IgE, or C5, can significantly increase the number of days the antigen experienced reduced levels of antigen as compared to an antibody without pH dependent binding.

Figure 12:
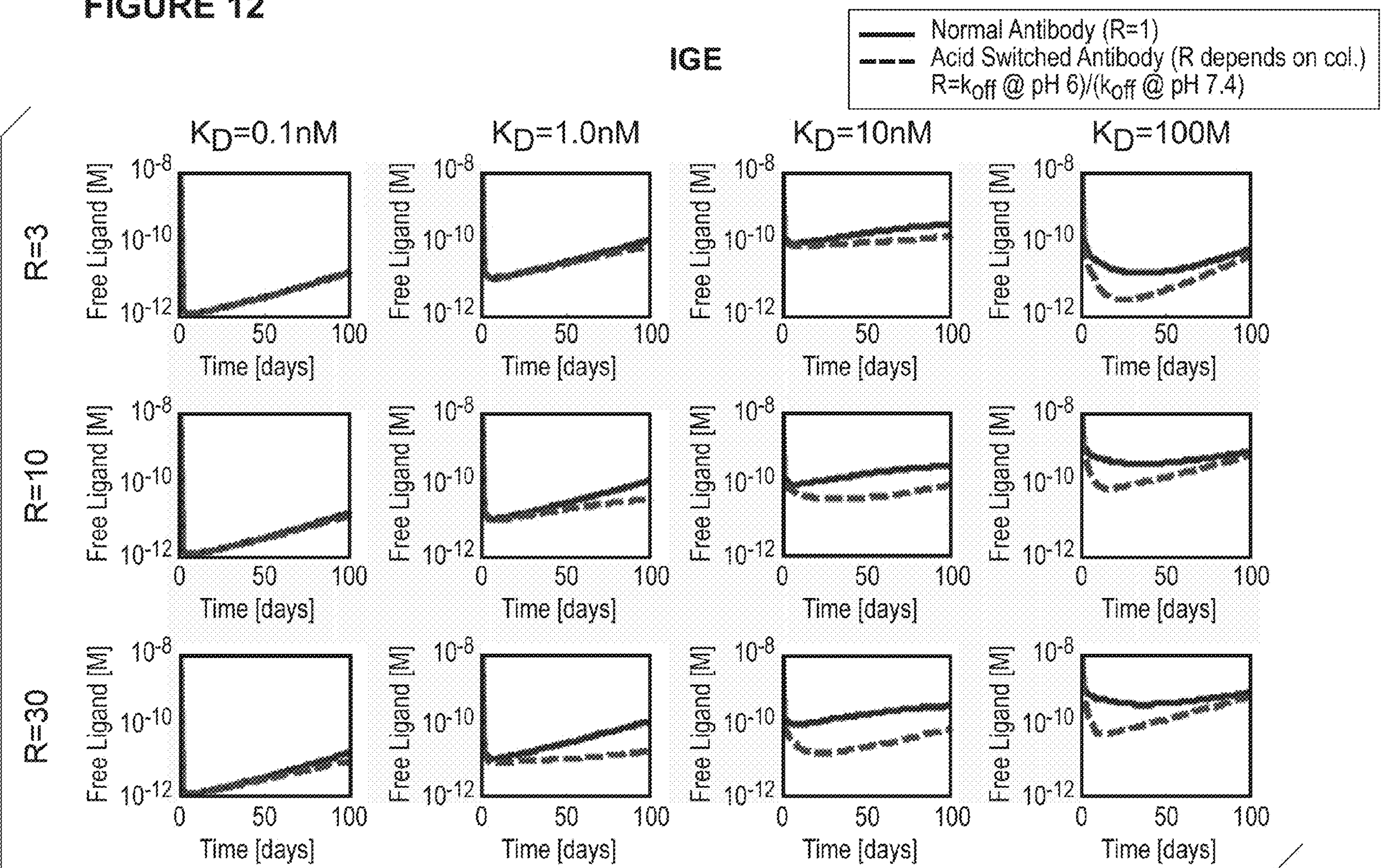

FIG. 12 models the time course for antigen concentration following administration of an antibody with pH dependent binding directed against antigen IgE.

Figure 13:
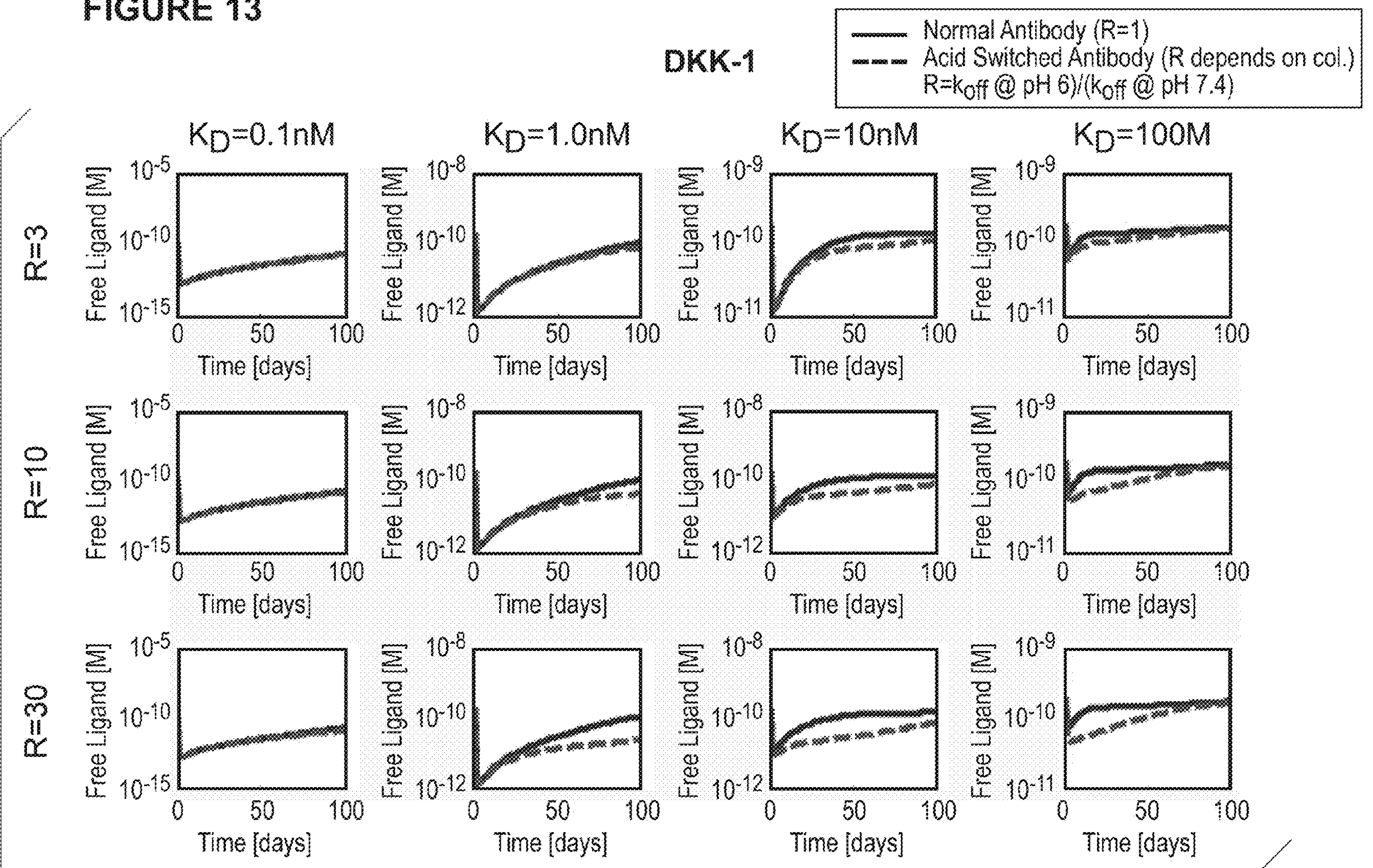

FIG. 13 models the time course for antigen concentration following administration of an antibody with pH dependent binding directed against antigen DKK1.

Figure 14:
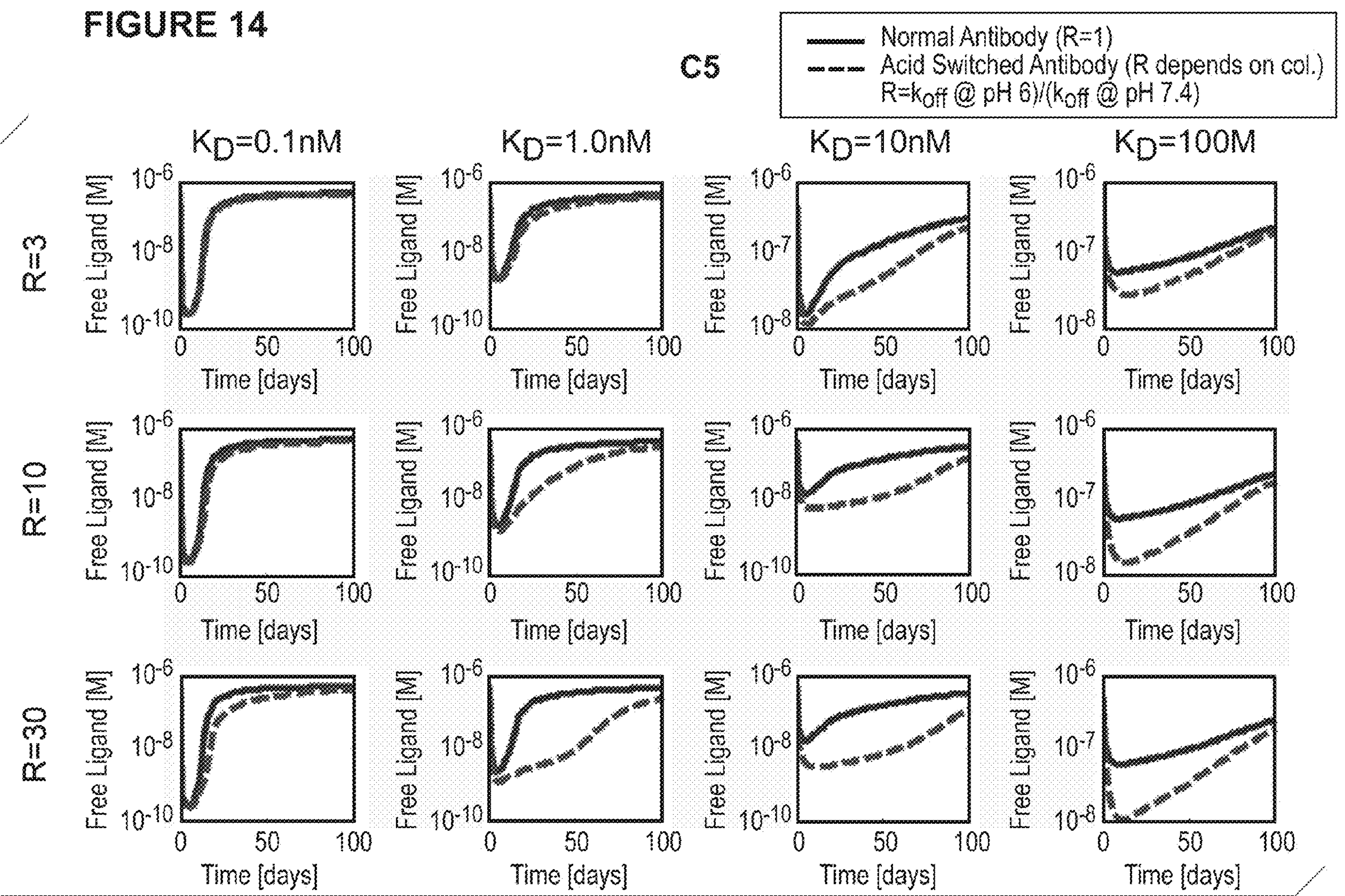

FIG. 14 models the time course for antigen concentration following administration of an antibody with pH dependent binding directed against antigen C5.

Figure 15:
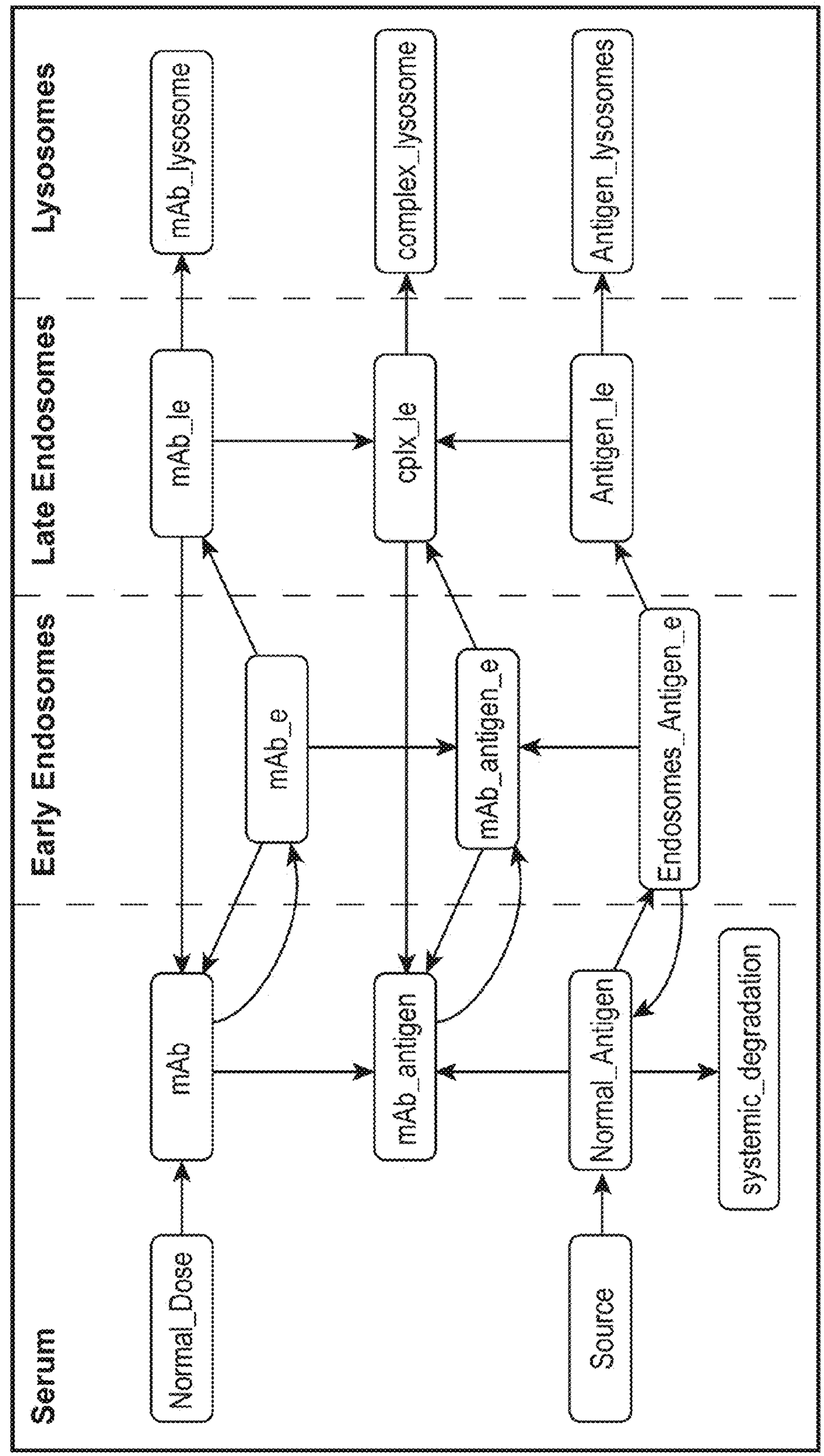

FIG. 15 details the trafficking model for antibodies with pH dependent binding used for modeling.

DETAILED DESCRIPTION OF THE INVENTION

The present invention relates to antibodies with pH dependent binding to its antigen such that the affinity for antigen binding at physiological pH (i.e., pH 7.4) is greater than at endosomal pH (i.e., pH 6.0 or 5.5). In other words, the $K_D$ or $k_{off}$ ratio at pH 5.5/pH 7.4 or at pH 6.0/pH 7.4 is more than, or ranges between, 2, 3, 4, 8, 10, 16, 20, 30, 40, or 100 or more. Such pH dependent antibodies preferentially dissociate from the antigen in the endosome. This can increase antibody half life in the circulation, as compared to antibodies with equivalent $K_D$s at pH 7.4 but with no pH dependent binding, when the antigen is one that undergoes antigen-mediated clearance (e.g., PCSK9). Antibodies with pH dependent binding can decrease the average total antigen half life when the antigen undergoes reduced clearance when bound to antibody (e.g., IL6). Antibodies with pH dependent binding can also prolong the decrease in antigen which is not antibody-bound. This can be important when antagonizing a target antigen typically present at high levels (e.g., IgE, DKK1, C5 and SOST). In addition, such antibodies can increase antigen half life when the antigen is a receptor and the receptor has increased clearance when bound to antibody (e.g, GMCSF receptor).

If the antigen mediates target-mediated degradation, then using such antibodies with pH dependent binding to achieve dissociation in the endosome can increase the pharmacodynamic effect of the antibody, for example, when the antigen undergoes target-mediated clearance (e.g., PCSK9). The antibody with pH dependent binding dissociates from the antigen, escapes antigen-mediated degradation, can recycle out of the cell via FcRn binding and will have a longer half-life than an antibody with similar $K_D$ at pH 7.4 but with no pH dependent binding.

Using such antibodies with pH dependent binding is also useful therapeutically when the soluble antigen is present at high concentration (e.g., IgE, C5, DKK1, or SOST). Upon dissociation from the antigen in the endosome and antigen degradation in the lysozome, the antibody can recycle into the plasma to bind additional free antigen, can prolong the decrease in non-antibody bound antigen, and can decrease the therapeutic dose required, as compared to an antibody with similar $K_D$ at pH 7.4 but without pH dependent binding.

Additionally, using antibodies with pH dependent binding can be useful when the antigen is present in membrane bound as well as soluble form, e.g., a receptor, and it is desired to enhance binding to the membrane bound form. By dissociating from the soluble form, the antibody has the increased opportunity to re-bind to the membrane form, increasing antibody in proximity to the cell membrane. If bound to the membrane form in a divalent manner, the effective affinity may be higher, or the effective dissociation rate may be slower, through the effect of avidity.

This has application for using antibody-drug conjugates (ADCs) when targeting an antigen present in both membrane-bound and soluble form. In FcRn-containing cells in the endothelium, soluble antigen will be cleared with the ADC recycling to the plasma compartment, allowing for opportunity to bind membrane bound antigen. With antibodies with pH dependent binding, increased binding to the membrane bound form, either divalently or monovalently, will cause increased antibody internalization with the membrane bound antigen and cell death. If bound to the receptor in a divalent matter, the avidity may increase the effective affinity or slow the effective rate of dissociation.

The mechanism for ADCC and complement dependent cytotoxicity (CDC) can also be exploited in using antibodies with pH dependent binding. In FcRn-containing cells in the endothelium, soluble antigen will be cleared and the ADC recycled to the plasma compartment, allowing for the opportunity to bind membrane-bound antigen. Liberating the antibodies from the soluble receptor will increase the free antibody available that can then bind to membrane bound antigen and increase cell killing.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also any antigen binding fragment thereof (i.e., "antigen-binding portion") or single chain thereof, fusion proteins comprising an antibody, and any other modified configuration of the immunoglobulin molecule that comprises an antigen recognition site, including, for example without limitation, single chain (scFv) and domain antibodies (e.g., human, camelid, or shark domain antibodies), maxibodies, minibodies, intrabodies, diabodies, triabodies, tetrabodies, vNAR and bis-scFv (see e.g., Hollinger and Hudson, Nature Biotech 23: 1126-1136, 2005). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody, as used herein, refers to one or more fragments of an intact antibody that retain the ability to specifically bind to a given antigen (e.g., target X). Antigen binding functions of an antibody can be performed by fragments of an intact antibody. Examples of binding fragments encompassed within the term "antigen binding portion" of an antibody include Fab, Fab', $F(ab')_2$, an Fd fragment consisting of the VH and CH1 domains, an Fv fragment consisting of the VL and VH domains of a single arm of an antibody, a single domain antibody (dAb) fragment (Ward et al., Nature 341:544-546, 1989), and an isolated complementarity determining region (CDR).

As used herein, the "CDRs" may be defined in accordance with any of Kabat, Chothia, extended, AbM, contact, and/or conformational definitions. The identity of the amino acid residues in a particular antibody that make up a CDR can be determined using methods well known in the art. As used herein, antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol. 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

As used herein, "humanized" antibody refers to forms of non-human (e.g., murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody.

As used herein, "human antibody" means an antibody having an amino acid sequence corresponding to that of an antibody that can be produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al. Monoclonal Antibodies and Cancer Therapy, Alan R. Liss, p. 77, 1985; Boerner et al., 1991, J. Immunol., 147 (1):86-95; and U.S. Pat. No. 5,750, 373.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al, 1997, J. Molec. Biol. 273:927-948). As used herein, a CDR may refer to CDRs defined by either approach or by a combination of both approaches.

As known in the art a "constant region" of an antibody refers to the constant region of the antibody light chain or the constant region of the antibody heavy chain, either alone or in combination.

As used herein, the term "PCSK9" refers to any form of PCSK9 and variants thereof that retain at least part of the activity of PCSK9. Unless indicated differently, such as by specific reference to human PCSK9, PCSK9 includes all mammalian species of native sequence PCSK9, e.g., human, canine, feline, equine, and bovine. One exemplary human PCSK9 is found as Uniprot Accession Number Q8NBP7.

As used herein, a "PCSK9 antagonist antibody" refers to an antibody that is able to inhibit PCSK9 biological activity and/or downstream pathway(s) mediated by PCSK9 signaling, including PCSK9-mediated down-regulation of the LDLR, and PCSK9-mediated decrease in LDL blood clearance. A pH dependent PCSK9 antagonist antibody encompasses antibodies that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "PCSK9 antagonist antibody" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and decreased blood LDL clearance), or the consequences of the biological activity, are substantially nullified, decreased, or neutralized in any meaningful degree. In some embodiments, a pH dependent PCSK9 antagonist antibody binds PCSK9 and prevents interaction with the LDLR. Examples of PCSK9 antagonist antibodies are provided herein.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O- allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An antibody "specifically binds" or "preferentially binds" to a target if it binds with greater affinity, avidity, more readily, and/or with greater duration than it binds to other substances. For example, an antibody that specifically or preferentially binds to a PCSK9 epitope is an antibody that binds this epitope with greater affinity, avidity, more readily, and/or with greater duration than it binds to other PCSK9 epitopes or non-PCSK9 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "non-signalling decoy" is a soluble receptor isoform or a binding protein that sequesters ligand from its cognate receptor(s).

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976 J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; CDC; Fc receptor binding; antibody-dependent cell-mediated cytotoxicity; phagocytosis; down-regulation of cell surface receptors (e.g., B cell receptor), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g., from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

By "Minimal Anticipated Biological Effect Level (MABEL)" is meant the minimal anticipated dose level leading to a minimal biological effect in humans. Safety factors are usually applied for the calculation for the first dose in man from MABEL. The calculation of MABEL should utilize all relevant in vitro and in vivo pharmacokinetic and pharmacodynamic information.

As used herein, "treatment" and "therapeutically effective" are approaches for obtaining beneficial or desired clinical results. For purposes of this invention related to pH dependent PCSK9 antagonist antibodies, beneficial or desired clinical results include, but are not limited to, one or more of the following: enhancement of LDL clearance and reducing incidence or amelioration of aberrant cholesterol and/or lipoprotein levels resulting from metabolic and/or eating disorders, or including familial hypercholesterolemia, atherogenic dyslipidemia, atherosclerosis, and, more generally, cardiovascular disease (CVD).

"Reducing incidence" means any of reducing severity (which can include reducing need for and/or amount of (e.g., exposure to) other drugs and/or therapies generally used for this condition. As is understood by those skilled in the art, individuals may vary in terms of their response to treatment, and, as such, for example, a "method of reducing incidence" reflects administering the pH dependent antibody based on a reasonable expectation that such administration may likely cause such a reduction in incidence in that particular individual.

"Ameliorating" means a lessening or improvement of one or more symptoms after administering a treatment as compared to not administering a treatment. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use of a pH dependent PCSK9 antagonist antibody, beneficial or desired results include clinical results such as reducing hypercholesterolemia or one or more symptoms of dyslipidemia, atherosclerosis, CVD, or coronary heart disease, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (i.e., univalent) and antigen.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Determinations of the association and dissociation rate constants, $k_a$ and $k_d$ respectively, to determine $K_D$ and $k_{off}$ ratios, are made using a surface plasmon resonance-based biosensor to characterize an analyte/ligand interaction under conditions where the analyte is monovalent with respect to binding a ligand that is immobilized at low capacity onto a sensor surface via a capture reagent. The analysis is performed using a kinetic titration methodology as described in Karlsson et al., Anal. Biochem 349, 136-147, 2006. The sensor chip, capturing reagent, and assay buffer employed for a given assay are chosen to give stable capture of ligand onto the sensor surface, minimize non-specific binding of the analyte to the surfaces, and yield analyte-binding responses that are appropriate for kinetic analysis, per the recommendations in Myszka, J. Mol. Recognit. 12, 279-284, 1999. The analyte-binding responses per analyte/ligand interaction are double referenced and fit to a 1:1 Langmuir "mass transport limited model" with $k_a$, $k_d$ and $R_{max}$ as global parameters as described in Myszka & Morton et al., *Biophys. Chem.* 64, 127-137 (1997). The equilibrium dissociation constant, $K_D$, is deduced from the ratio of the kinetic rate constants, $K_D=k_d/k_a$. Such determinations preferably take place at 25° C. or 37° C.

A. Methods for Preventing or Treating Disorders

In one aspect regarding pH dependent PCSK9 antagonist antibodies, the invention provides a method for treating or preventing hypercholesterolemia, and/or at least one symptom of dyslipidemia, atherosclerosis, CVD or coronary heart disease, in an individual comprising administering to the individual an effective amount of a PH dependent pH dependent PCSK9 antagonist antibody that antagonizes circulating PCSK9.

In a further aspect, the invention provides an effective amount of a pH dependent PCSK9 antagonist antibody that antagonizes circulating PCSK9 for use in treating or preventing hypercholesterolemia, and/or at least one symptom of dyslipidemia, atherosclerosis, CVD or coronary heart disease, in an individual. The invention further provides the use of an effective amount of a pH dependent PCSK9 antagonist antibody that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

Advantageously, therapeutic administration of the antibody results in lower blood cholesterol and/or lower blood LDL. Preferably, blood cholesterol and/or blood LDL is at least about 10% or 15% lower than before administration. More preferably, blood cholesterol and/or blood LDL is at least about 20% lower than before administration of the antibody. Yet more preferably, blood cholesterol and/or blood LDL is at least 30% lower than before administration of the antibody. Advantageously, blood cholesterol and/or blood LDL is at least 40% lower than before administration of the antibody. More advantageously, blood cholesterol and/or blood LDL is at least 50% lower than before administration of the antibody. Very preferably, blood cholesterol and/or blood LDL is at least 60% lower than before administration of the antibody. Most preferably, blood cholesterol and/or blood LDL is at least 70% lower than before administration of the antibody.

With respect to all methods described herein, reference to pH dependent antibodies against any appropriate antigen also includes compositions comprising one or more additional agents. These compositions may further comprise suitable excipients, such as pharmaceutically acceptable excipients including buffers, which are well known in the art. The present invention can be used alone or in combination with other conventional methods of treatment.

The pH dependent antibody can be administered to an individual via any suitable route. It should be apparent to a person skilled in the art that the examples described herein are not intended to be limiting but to be illustrative of the techniques available. Accordingly, in some embodiments, the pH dependent antibody is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, pH dependent antibody can be aerosolized using a fluorocarbon formulation and a metered dose inhaler, or inhaled as a lyophilized and milled powder.

In one embodiment, a pH dependent antibody is administered via site-specific or targeted local delivery techniques. Examples of site-specific or targeted local delivery techniques include various implantable depot sources of the pH dependent antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publ. No. WO 00/53211 and U.S. Pat. No. 5,981,568.

Various formulations of a pH dependent antibody may be used for administration. In some embodiments, the pH dependent antibody may be administered neat. In some embodiments, pH dependent antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy, 20th Ed., Mack Publishing (2000).

These agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Antibodies with pH dependent binding can also be administered via inhalation, as described herein. Generally, for administration of pH dependent antibodies, an initial candidate dosage can be about 2 mg/kg. For the purpose of the present invention, a typical daily dosage might range from about any of about 3 μg/kg to 30 μg/kg to 300 μg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce blood LDL levels. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the antibody used) can vary over time.

For the purpose of the present invention, the appropriate dosage of a pH dependent antibody will depend on the antibody (or compositions thereof) employed, the type and severity of symptoms to be treated, whether the agent is administered for preventive or therapeutic purposes, previous therapy, the patient's clinical history and response to the agent, the patient's blood antigen levels, the patient's synthesis and clearance rate for antigen, the patient's clearance rate for the administered agent, and the discretion of the attending physician. Typically the clinician will administer a pH dependent antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., hypercholesterolemia. Alternatively, sustained continuous release formulations of antibodies may be appropriate. Various formulations and devices for achieving sustained release are known in the art.

In one embodiment, dosages for an antagonist antibody may be determined empirically in individuals who have been given one or more administration(s) of an antagonist antibody. Individuals are given incremental dosages of a antibody. To assess efficacy, an indicator of the disease can be followed.

Administration of a pH dependent antibody in accordance with the method in the present invention can be continuous or intermittent, depending, for example, upon the recipient's physiological condition, whether the purpose of the administration is therapeutic or prophylactic, and other factors known to skilled practitioners. The administration of a pH dependent antibody may be essentially continuous over a preselected period of time or may be in a series of spaced doses.

In some embodiments, more than one antagonist antibody may be present. At least one, at least two, at least three, at least four, at least five different, or more antagonist antibodies and/or peptides can be present. Generally, those antibodies or peptides may have complementary activities that do not adversely affect each other. A pH dependent antibody can also be used in conjunction with other therapeutics. A pH dependent antibody can also be used in conjunction with other agents that serve to enhance and/or complement the effectiveness of the agents.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing the pH dependent antibody are prepared by methods known in the art, such as described in Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic pH dependent antibody compositions are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a pH dependent antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

B. pH Dependent Antibodies

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), human antibodies, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the pH dependent antibody is a monoclonal antibody. The pH dependent antibody can also be humanized. In other embodiments, the antibody is human.

In some embodiments, the antibody comprises a modified constant region, such as a constant region that is immunologically inert, that is, having a reduced potential for provoking an immune response. In some embodiments, the constant region is modified as described in Eur. J. Immunol., 1999, 29:2613-2624; PCT Publ. No. WO99/58572; and/or UK Patent Application No. 9809951.8. The Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type IgG2 sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

One way of determining binding affinity of antibodies to antigen is by measuring binding affinity of monofunctional Fab fragments of the antibody. To obtain monofunctional Fab fragments, an antibody (for example, IgG) can be cleaved with papain or expressed recombinantly. The affinity of a Fab fragment of an antibody can be determined by surface plasmon resonance (Biacore3000™ surface plasmon resonance (SPR) system, Biacore, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated antigen can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of antigen on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B., 1994. Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any antigen, including human or another mammalian species (such as mouse, rat, primate). Binding affinity of an antibody is generally measured at 25° C., but can also be measured at 37° C.

The antibodies may be made by any method known in the art. The route and schedule of immunization of the host animal are generally in keeping with established and conventional techniques for antibody stimulation and production, as further described herein. General techniques for production of human and mouse antibodies are known in the art and/or are described herein. For pH dependent antibodies against PCSK9, a currently preferred method of making the antibodies comprises the immunization of PCSK9 knockout (PCSK9−/−) animals as disclosed herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., 1982, In Vitro, 18:377-381. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the PCSK9 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as a source of antibodies encompass all derivatives, progeny cells of the parent hybridomas that produce monoclonal antibodies specific for PCSK9, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human PCSK9, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups, can yield a population of antibodies (e.g., monoclonal antibodies).

Once antibodies are generated or selected, the antibodies can be optimized for pH dependent binding, for example, as disclosed in Example 1 herein.

If desired, the pH dependent antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g., Tiller et al., 2008, J. Immunol. Methods 329, 112; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to antigen and greater efficacy. It will be apparent to one of skill in the art that one or more polynucleotide changes can be made to the pH dependent antibody and still maintain its antigen binding ability.

There are four general steps to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated CDRs fused to human constant domains. See, for example, Winter et al., 1991, Nature 349:293-299; Lobuglio et al., 1989, Proc. Nat. Acad. Sci. USA 86:4220-4224; Shaw et al., 1987, J. Immunol. 138:4534-4538; and Brown et al., 1987, Cancer Res. 47:3577-3583. Other references describe rodent CDRs grafted into a human supporting framework region (FR) prior to fusion with an appropriate human antibody constant domain. See, for example, Riechmann et al., 1988, Nature 332:323-327; Verhoeyen et al., 1988, Science 239:1534-1536; and Jones et al., 1986, Nature 321:522-525. Another reference describes rodent CDRs supported by recombinantly engineered rodent framework regions. See, for example, European Patent Publ. No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g., PCT Publ. No. WO99/58572; UK Patent Application No. 9809951.8. Other methods of humanizing antibodies that may also be utilized are disclosed by Daugherty et al., 1991, Nucl. Acids Res. 19:2471-2476 and in U.S. Pat. Nos. 6,180,377; 6,054,297; 5,997,867; 5,866,692; 6,210,671; and 6,350,861; and in PCT Publ. No. WO 01/27160.

In yet another alternative, fully human antibodies may be obtained by using commercially available mice that have been engineered to express specific human immunoglobulin proteins. Transgenic animals that are designed to produce a more desirable or more robust immune response may also be used for generation of humanized or human antibodies. Examples of such technology are Xenomouse™ from Abgenix, Inc. (Fremont, Calif.), HuMAb-Mouse® and TC Mouse™ from Medarex, Inc. (Princeton, N.J.), and the VelocImmune0 mouse from Regeneron Pharmaceuticals, Inc. (Tarrytown, N.Y.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., 1994, Annu. Rev. Immunol. 12:433-455. Alternatively, the phage display technology (McCafferty et al., 1990, Nature 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; see, e.g., Johnson, Kevin S, and Chiswell, David J., 1993, Current Opinion in Structural Biology 3:564-571. Several sources of V-gene segments can be used for phage display. Clackson et al., 1991, Nature 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992, Bio/Technol. 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., 1993, Nucl. Acids Res. 21:2265-2266. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publ. No. WO 93/06213). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, 2001, et al. Vaccine 19:2756; Lonberg, N. and D. Huszar, 1995, Int. Rev. Immunol 13:65; and Pollock, et al., 1999, J Immunol Methods 231:147. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for the desired antigen.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publ. No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publ. No. WO 87/04462. The DNA also may be modified, for example, by substituting the coding sequence for human heavy and light chain constant domains in place of the homologous murine sequences, Morrison et al., 1984, Proc. Nat. Acad. Sci. 81:6851, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

pH dependent antibodies and polypeptides derived from antibodies can be identified or characterized using methods known in the art, whereby reduction, amelioration, or neutralization of biological activity is detected and/or measured. In some embodiments, a pH dependent antibody or polypeptide is identified by incubating a candidate agent with antigen and monitoring binding and/or attendant reduction or neutralization of a biological activity. The binding assay may be performed with purified antigen polypeptide(s), or with cells naturally expressing, or transfected to express, to polypeptide(s). In one embodiment, the binding assay is a competitive binding assay, where the ability of a candidate antibody to compete with a known antagonist for binding is evaluated. The assay may be performed in various formats, including the ELISA format. In other embodiments, a pH dependent antibody is identified by incubating a candidate agent with the antigen and monitoring binding and attendant inhibition of LDLR expression and/or blood cholesterol clearance.

Following initial identification, the activity of a candidate pH dependent antibody can be further confirmed and refined by bioassays that are known to test the targeted biological activities. Alternatively, bioassays can be used to screen candidates directly. Some of the methods for identifying and characterizing antibodies, peptides, or aptamers are described in detail in the Examples.

Antibodies with pH dependent binding may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, (Cold Spring Harbor Laboratory Press, Cold Spring Harbor, N.Y., 1999). In an additional example, epitope mapping can be used to determine the sequence to which a pH dependent antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an antibody. In another example, the epitope to which the pH dependent antibody binds can be determined in a systematic screening by using overlapping peptides derived from the antigen sequence and determining binding by the antibody. According to the gene fragment expression assays, the open reading frame encoding the antigen is fragmented either randomly or by specific genetic constructions and the reactivity of the expressed fragments of antigen with the antibody to be tested is determined. The gene fragments may, for example, be produced by PCR and then transcribed and translated into protein in vitro, in the presence of radioactive amino acids. The binding of the antibody to the radioactively labeled fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant antigen in which various fragments of the polypeptide have been replaced (swapped) with sequences from antigen from another species, or a closely related, but antigenically distinct protein (such as another member of the proprotein convertase family). By assessing binding of the antibody to the mutant antigen, the importance of the particular antigen fragment to antibody binding can be assessed.

Yet another method which can be used to characterize a pH dependent antibody is to use competition assays with other antibodies known to bind to the same antigen to determine if the pH dependent antibody binds to the same epitope as other antibodies. Competition assays are well known to those of skill in the art.

An expression vector can be used to direct expression of a pH dependent antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., 1993, Trends Biotechnol. 11:202; Chiou et al., 1994, Gene Therapeutics: Methods And Applications Of Direct Gene Transfer (J. A. Wolff, ed.); Wu et al., 1988, J. Biol. Chem. 263:621; Wu et al., 1994, J. Biol. Chem. 269:542; Zenke et al., 1990, Proc. Natl. Acad. Sci. USA 87:3655; Wu et al., 1991, J. Biol. Chem. 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, 1994, Cancer Gene Therapy 1:51; Kimura, 1994, Human Gene Therapy 5:845; Connelly, 1995, Human Gene Therapy 1:185; and Kaplitt, 1994, Nature Genetics 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publ. Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publ. Nos. WO 94/12649, WO 93/03769; WO 93/19191; WO 94/28938; WO 95/11984 and WO 95/00655). Administration of DNA linked to killed adenovirus as described in Curiel, 1992, Hum. Gene Ther. 3:147, can also be employed.

Non-viral delivery vehicles and methods can also be employed, including, but not limited to, polycationic condensed DNA linked or unlinked to killed adenovirus alone (see, e.g., Curiel, 1992, Hum. Gene Ther. 3:147); ligand-linked DNA (see, e.g., Wu, J., 1989, Biol. Chem. 264:16985); eukaryotic cell delivery vehicles cells (see, e.g., U.S. Pat. No. 5,814,482; PCT Publ. Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publ. No. WO 90/11092 and U.S. Pat. No. 5,580,859. Liposomes that can act as gene delivery vehicles are described in U.S. Pat. No. 5,422,120; PCT Publ. Nos. WO 95/13796; WO 94/23697; WO 91/14445; and EP 0524968. Additional approaches are described in Philip, 1994, Mol. Cell. Biol., 14:2411, and in Woffendin, 1994 Proc. Natl. Acad. Sci. 91:1581.

This invention encompasses compositions, including pharmaceutical compositions, comprising antibodies described herein or made by the methods and having the characteristics described herein. As used herein, compositions comprise one or more pH dependent antibody, and/or one or more polynucleotides comprising sequences encoding one or more these antibodies. These compositions may further comprise suitable excipients, such as pharmaceutically acceptable excipients including buffers, which are well known in the art.

The invention also provides CDR portions of pH dependent antibodies (including Chothia and Kabat CDRs). Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies and peptides can be made recombinantly using procedures that are well known in the art. In one embodiment, a polynucleotide comprises a sequence encoding the heavy chain and/or the light chain variable regions of antibody 4A5, 5A10, 6F6, 7D4 or L1L3. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide. Bird et al., 1988, Science 242:423-426. An example of a linking peptide is $(GGGGS)_3$ (SEQ ID NO:22), which bridges approximately 3.5 nm between the carboxy terminus of one variable region and the amino terminus of the other variable region. Linkers of other sequences have been designed and used. Bird et al., 1988, supra. Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publ. No. WO 94/04690.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publ. Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibodies 5A10 or 7D4 or one or more CDRs derived from antibodies 5A10 or 7D4 can be made, for example, using any methods know in the art. For example, four general steps may be used to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) using the actual humanizing methodologies/techniques; and (4) transfecting and expressing the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

In the recombinant humanized antibodies, the Fc portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

Humanized antibody comprising the light or heavy chain variable regions or one or more CDRs of an antibody or its variants, or one or more CDRs derived from the antibody or its variants, can be made using any methods known in the art.

Humanized antibodies may be made by any method known in the art.

The invention encompasses modifications to the antibodies and polypeptides of the invention, including functionally equivalent antibodies which do not significantly affect their properties and variants which have enhanced or decreased activity and/or affinity. For example, the amino acid sequence may be mutated to obtain an antibody with the desired binding affinity to its antigen. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions." If such substitutions result in a change in biological activity, then more substantial changes, denominated "exemplary substitutions", or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) Non-polar: Norleucine, Met, Ala, Val, Leu, Ile; (2) Polar without charge: Cys, Ser, Thr, Asn, Gln; (3) Acidic (negatively charged): Asp, Glu; (4) Basic (positively charged): Lys, Arg; (5) Residues that influence chain orientation: Gly, Pro; and (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect ADCC. In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate ADCC, or does not activate microglia; or have reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., 1995, Immunology 86:319-324; Lund et al., 1996, J. Immunology 157:4963-9 157:4963-4969; Idusogie et al., 2000, J. Immunology 164:4178-4184; Tao et al., 1989, J. Immunology 143: 2595-2601; and Jefferis et al., 1998, Immunological Reviews 163:59-76. In some embodiments, the constant region is modified as described in Eur. J. Immunol., 1999, 29:2613-2624; PCT Publ. No. WO99/58572; and/or UK Patent Application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., 1989, J. Immunology 143: 2595-2601; and Jefferis et al., 1998, Immunological Reviews 163: 59-76. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publ. No. WO 99/58572. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publ. No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed “library scanning mutagenesis”. Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore surface plasmon resonance analysis, which detects differences in binding affinity of about 2-fold or greater. Biacore is particularly useful when the starting antibody already binds with a relatively high affinity, for example a $K_D$ of about 10 nM or lower. Screening using Biacore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, screening, and selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid, and may further include additional substitutions at that position, depending on the complexity of the library that is desired, or permitted using the desired screening or selection method. In addition, if desired, and adjacent amino acid position can be randomized to at least two or more amino acids. Randomization of adjacent amino acids may permit additional conformational flexibility in the mutant CDR, which may, in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

The invention also encompasses fusion proteins comprising one or more fragments or regions from the antibodies or polypeptides of this invention. In one embodiment, a fusion polypeptide is provided that comprises at least 10 contiguous amino acids of a variable light chain region shown in SEQ ID NO: 3 and/or at least 10 amino acids of a variable heavy chain region shown in SEQ ID NOs: 4 or 5. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies or polypeptides conjugated (for example, linked) to an agent that facilitate coupling to a solid support (such as biotin or avidin). For simplicity, reference will be made generally to antibodies with the understanding that these methods apply to any of the antigen binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent such as a fluorescent molecule, a radioactive molecule or any others labels known in the art. Labels are known in the art which generally provide (either directly or indirectly) a signal.

The invention also provides compositions (including pharmaceutical compositions) and kits comprising, as this disclosure makes clear, any or all of the antibodies and/or polypeptides described herein.

The invention also provides isolated polynucleotides encoding the antibodies and peptides of the invention, and vectors and host cells comprising the polynucleotide.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as pharmaceutical compositions) comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies or polypeptides described herein. In still other embodiments, the composition comprises either or both of the polynucleotides shown in SEQ ID NO: 23 and SEQ ID NO: 24. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure (National Biomedical Research Foundation, Washington D.C.), Vol. 5, Suppl. 3, pp. 345-358; Hein J., 1990, Unified Approach to Alignment and Phylogenes pp. 626-645 Methods in Enzymology vol. 183, (Academic Press, Inc., San Diego, Calif.); Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy (Freeman Press, San Francisco, Calif.); Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein.

One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989, supra.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al., 1994, eds. (Birkauswer Press, Boston, Mass.).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publ. No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but are not limited to COS, HeLa, NSO, and CHO cells. See also PCT Publ. No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to antigen is effected by an immunoassay or FACS. A cell overexpressing the antibody or protein of interest can be identified.

C. Compositions

The compositions used in the methods of the invention comprise an effective amount of a pH dependent antibody, or a pH dependent antibody derived polypeptide, described herein. Examples of such compositions, as well as how to formulate them, are also described in an earlier section and below. In one embodiment, the composition comprises one or more pH dependent antibodies. In other embodiments, the pH dependent antibody recognizes human PCSK9. In still other embodiments, the pH dependent antibody is humanized. In yet other embodiments, the pH dependent antibody comprises a constant region that does not trigger an unwanted or undesirable immune response, such as antibody-mediated lysis or ADCC. In other embodiments, the pH dependent antibody comprises one or more CDR(s) of the antibody (such as one, two, three, four, five, or, in some embodiments, all six CDRs). In some embodiments, the pH dependent antibody is human.

The composition used in the present invention can further comprise pharmaceutically acceptable carriers, excipients, or stabilizers (Remington: The Science and Practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

In one embodiment, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate.

The pH dependent antibody and compositions thereof can also be used in conjunction with other agents that serve to enhance and/or complement the effectiveness of the agents.

D. Kits

The invention also provides kits for use in the instant methods. Kits of the invention include one or more containers comprising a pH dependent antibody (such as a humanized antibody) or peptide described herein and instructions for use in accordance with any of the methods of the invention described herein. Generally, these instructions comprise a description of administration of the pH dependent antibody for the above described therapeutic treatments.

In some embodiments, the antibody is a humanized antibody. In some embodiments, the antibody is human. In other embodiments, the antibody is a monoclonal antibody. The instructions relating to the use of a pH dependent antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a pH dependent antibody. The container (e.g., pre-filled syringe or autoinjector) may further comprise a second pharmaceutically active agent.

Kits may optionally provide additional components such as buffers and interpretive information. Normally, the kit comprises a container and a label or package insert(s) on or associated with the container.

Mutations and Modifications

To express the antibodies of the present invention, DNA fragments encoding $V_H$ and $V_L$ regions can first be obtained using any of the methods described above. Various modifications, e.g., mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant domain of an antibody. In some embodiments, the cysteine is canonical.

The antibodies may also be modified, e.g., in the variable domains of the heavy and/or light chains, e.g., to alter a binding property of the antibody. For example, a mutation may be made in one or more of the CDR regions to increase or decrease the $K_D$ of the antibody for antigen, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant domain to increase the half-life of a pH dependent. See, e.g., PCT Publ. No. WO 00/09560. A mutation in a framework region or constant domain can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant domain.

In a process known as "germlining", certain amino acids in the $V_H$ and $V_L$ sequences can be mutated to match those found naturally in germline $V_H$ and $V_L$ sequences. In particular, the amino acid sequences of the framework regions in the $V_H$ and $V_L$ sequences can be mutated to match the germline sequences to reduce the risk of immunogenicity when the antibody is administered. Germline DNA sequences for human $V_H$ and $V_L$ genes are known in the art (see e.g., the "Vbase" human germline sequence database; see also Kabat, E. A., et al. (1991) Sequences of Proteins of Immunological Interest, Fifth Edition, U.S. Department of Health and Human Services, NIH Publ. No. 91-3242; Tomlinson et al., 1992, J. Mol. Biol. 227:776-798; and Cox et al., 1994, Eur. J. Immunol. 24:827-836.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution eliminates asparagine-glycine pairs, which form potential deamidation sites, by altering one or both of the residues. In another example, the C-terminal lysine of the heavy chain of a pH dependent antibody of the invention can be cleaved. In various embodiments of the invention, the heavy and light chains of the antibodies may optionally include a signal sequence.

Once DNA fragments encoding the $V_H$ and $V_L$ segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publ. No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain $CH_1$ constant region. The CH1 heavy chain constant region may be derived from any of the heavy chain genes.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991, Sequences of Proteins of Immunological Interest, Fifth Edition, U.S. Department of Health and Human Services, NIH Publ. No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to antigen and to another molecule.

In another embodiment, a fusion antibody or immunoadhesin may be made that comprises all or a portion of an antibody of the invention linked to another polypeptide. In another embodiment, only the variable domains of the antibody are linked to the polypeptide. In another embodiment, the $V_H$ domain of an antibody is linked to a first polypeptide, while the $V_L$ domain of an antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another. The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other embodiments, other modified antibodies may be prepared using pH dependent antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., 1993, Proc. Natl. Acad. Sci. USA 90:6444-6448), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. In addition, bispecific antibodies may be formed as "diabodies" or "Janusins." In some embodiments, the bispecific antibody binds to two different epitopes of antigen. In some embodiments, the modified antibodies described above are prepared using one or more of the variable domains or CDR regions from a human antibody provided herein.

Generation of Antigen-Specific Antibodies

DNA of the heavy and light chains of representative antibodies of the present invention, 5L1721H23_6L3 and 5L1721H23_6L3H3, were deposited in the American Type Culture Collection (ATCC) (under the terms of the Budapest Treaty) on Dec. 22, 2009, and were assigned the accession numbers in Table 2. All restrictions on the availability to the public of the plasmids so deposited will be irrevocably removed upon the issuance of a patent from the specification of the present invention. The antibody references for the heavy and light chains of 5L1721H23_6L3 are UC-H5H23 and UC-H5L1721-6L3, respectively. The antibody references for the heavy and light chains of 5L1721H23_6L3H3 are UC-H5H23-6H3 and UC-H5L1721-6L3, respectively.

TABLE 2

| Antibody Reference | ATCC Accession No. |
|---|---|
| UC-H5H23 | PTA-10547 |
| UC-H5H23-6H3 | PTA-10548 |
| UC-H5L1721-6L3 | PTA-10549 |

EXAMPLES

Example 1

Modeling Antibody pH Dependent Binding to PCSK9 Antigen

Computer modeling was used to predict whether an antibody with pH dependent antigen binding could impact antibody half life the duration of the lowering of the PCSK9 serum concentration. For the purpose of this modeling the following assumptions were made: 1 uM dose of antibody in blood; 21 day (non pH dependent) antibody half-life; a simulation run duration of 100 days; for the pH dependent antibody, a $K_{on}$=1e5/M/s, a $K_{off}$ @ neutral pH=$K_D$*$K_{on}$, the pH dependent binding is modeled as an increase in $K_{off}$ in the acidic endosomes; and $K_{off}$ at acidic pH=R*$K_{off}$ at neutral pH.

The time rates of change of the species in the model are specified in terms of model parameters by the differential equations below. Generally, the model is allowed to proceed with antibody levels set to zero until it reaches a steady state; at that time, a bolus of antibody is simulated by resetting [mAb] from zero to a level reflective of the dose, and then allowing the model described below to proceed.

$$[P]' = k_{P,create} - k_{activeuptake}[P] - k_{protein,on}[LDLR][P] + k_{P,off}[P\cdot LDLR] - k_{protein,on}[LDL\cdot LDLR][P] + k_{P,off}[LDL\cdot P\cdot LDLR] - 2k_{on,neutral}[mAb][P] + k_{off,neutral}[mAb\cdot P] - k_{on,neutral}[mAb\cdot P][P] + 2k_{off,neutral}[mAb\cdot P\cdot P] - \frac{k_{endouptake}[P] - k_{endouptake}A[P]_{early}}{V}$$

$$[LDL]' = k_{L,create} - k_{L,clear}[LDL] - k_{protein,on}[LDLR][LDL] + k_{L,off}[LDL\cdot LDR] - k_{protein,on}[P\cdot LDLR][LDL] + k_{L,off}[LDL\cdot P\cdot LDLR]$$

$$[LDLR]' = k_{R,create} - k_{R,clear}[LDLR] - k_{protein,on}[LDLR][LDL] + k_{L,off}[LDL\cdot LDLR] - k_{protein,on}[LDLR][P] + k_{P,off}[P\cdot LDLR] + k_{recycle}[LDL\cdot LDLR]_{in}$$

$$[mAb]' = -2k_{on,neutral}[mAb][P] + k_{off,neutral}[mAb\cdot P] - \frac{k_{endouptake}[mAb] - k_{endouptake}A[mAb]_{early}}{V} + \frac{k_{endouptake}(1-A)F[mAb]_{late}}{V} + \frac{\alpha k_{endouptake}(1-A)F[mAb]_{active}}{V}$$

$$[mAb\cdot P]' = 2k_{on,neutral}[mAb][P] - k_{off,neutral}[mAb\cdot P] - k_{on,neutral}[mAb\cdot P][P] + 2k_{off,neutral}[mAb\cdot P\cdot P] - \frac{k_{endouptake}[mAb\cdot P] - k_{endouptake}A[mAb\cdot P]_{early}}{V} + \frac{k_{endouptake}(1-A)F[mAb\cdot P]_{late}}{V} - k_{activeuptake}[mAb\cdot P]$$

$$[mAb\cdot P\cdot P]' = k_{on,neutral}[mAb\cdot P][P] - 2k_{off,neutral}[mAb\cdot P\cdot P] - \frac{k_{endouptake}[mAb\cdot P\cdot P] - k_{endouptake}A[mAb\cdot P\cdot P]_{early}}{V} + \frac{k_{endouptake}(1-A)F[mAb\cdot P\cdot P]_{late}}{V} - 2k_{activeuptake}[mAb\cdot P\cdot P]$$

$$[LDL\cdot LDLR]' = k_{protein,on}[LDLR][LDL] - k_{L,off}[LDL\cdot LDLR] - k_{protein,on}[LDL\cdot LDLR][P] + k_{P,off}[LDL\cdot P\cdot LDLR] - k_{internalize}[LDL\cdot LDLR]$$

$$[P\cdot LDLR]' = k_{protein,on}[LDLR][P] - k_{P,off}[P\cdot LDLR] - k_{protein,on}[P\cdot LDLR][LDL] + k_{L,off}[LDL\cdot P\cdot LDLR] - k_{internalize}[P\cdot LDLR]$$

$$[LDL\cdot P\cdot LDLR]' = k_{protein,on}[LDL\cdot LDLR][P] - k_{P,off}[LDL\cdot P\cdot LDLR] + k_{protein,on}[P\cdot LDLR][LDL] - k_{L,off}[LDL\cdot P\cdot LDLR] - k_{internalize}[LDL\cdot P\cdot LDLR]$$

$$[P\cdot LDLR]'_{in} = k_{internalize}[P\cdot LDLR] - k_{recycle}[P\cdot LDLR]$$

$$\{LDL\cdot LDLR]'_{in} = k_{internalize}[LDL\cdot LDLR] - k_{recycle}[LDL\cdot LDLR]_{in}$$

$$[LDL\cdot P\cdot LDLR]'_{in} = k_{internalize}[LDL\cdot P\cdot LDLR] - k_{recycle}[LDL\cdot P\cdot LDLR]_{in}$$

$$[mAb]'_{early} = \frac{k_{endouptake}[mAb] - k_{endouptake}A[mAb]_{early}}{V_{early}} - 2k_{on,neutral}[mAb]_{early}[P]_{early} + k_{off,neutral}[mAb\cdot P]_{early} - \frac{k_{endouptake}(1-A)[mAb]_{early}}{V_{early}}$$

$$[P]'_{early} = \frac{k_{endouptake}[P] - k_{endouptake}A[P]_{early}}{V_{early}} - 2k_{on,neutral}[mAb]_{early}[P]_{early} + k_{off,neutral}[mAb\cdot P]_{early} - k_{on,neutral}[mAb\cdot P]_{early} + 2k_{off,neutral}[mAb\cdot P\cdot P]_{early} - \frac{k_{endouptake}(1-A)[P]_{early}}{V_{early}}$$

-continued $$[mAb\cdot P]'_{early} = \frac{k_{endouptake}[mAb\cdot P] - k_{endouptake}A[mAb\cdot P]_{early}}{V_{early}} + 2k_{on,neutral}[mAb]_{early}[P]_{early} - k_{off,neutral}[mAb\cdot P]_{early} - k_{on,neutral}[mAb\cdot P]_{early}[P]_{early} + 2k_{off,neutral}[mAb\cdot P\cdot P]_{early} - \frac{k_{endouptake}(1-A)[mAb\cdot P]_{early}}{V_{early}}$$

$$[mAb\cdot P\cdot P]'_{early} = \frac{k_{endouptake}[mAb\cdot P\cdot P] - k_{endouptake}A[mAb\cdot P\cdot P]_{early}}{V_{early}} + k_{on,neutral}[mAb\cdot P]_{early}[P]_{early} - 2k_{off,neutral}[mAb\cdot P\cdot P]_{early} - \frac{k_{endouptake}(1-A)[mAb\cdot P\cdot P]_{early}}{V_{early}}$$

$$[mAb]'_{late} = \frac{k_{endouptake}(1-A)[mAb]_{early}}{V_{late}} - 2k_{on,acidic}[mAb]_{late}[P]_{late} + k_{off,acidic}[mAb\cdot P]_{late} - \frac{k_{endouptake}(1-A)(1-F)[mAb]_{late}}{V_{late}}$$

$$[P]'_{late} = \frac{k_{endouptake}(1-A)[P]_{early}}{V_{late}} - 2k_{on,acidic}[mAb]_{late}[P]_{late} + k_{off,acidic}[mAb\cdot P]_{late} - k_{on,acidic}[mAb\cdot P]_{late}[P]_{late} + 2k_{off,acidic}[mAb\cdot P\cdot P]_{late} - \frac{k_{endouptake}(1-A)[P]_{late}}{V_{late}}$$

$$[mAb\cdot P]'_{late} = \frac{k_{endouptake}(1-A)[mAb\cdot P]_{early}}{V_{late}} + 2k_{on,acidic}[mAb]_{late}[P]_{late} - k_{off,acidc}[mAb\cdot P]_{late} - k_{on,acidic}[mAb\cdot P]_{late} + 2k_{off,acidic}[mAb\cdot P\cdot P]_{late} - \frac{k_{endouptake}(1-A)F[mAb\cdot P]_{late}}{V_{late}} - \frac{k_{endouptake}(1-A)(1-F)[mAb\cdot P]_{late}}{V_{late}}$$

$$[mAb\cdot P\cdot P]'_{late} = \frac{k_{endouptake}(1-A)[mAb\cdot P\cdot P]_{early}}{V_{late}} + k_{on,acidic}[mAb\cdot P]_{late}[P]_{late} - 2k_{off,acidic}[mAb\cdot P\cdot P]_{late} - \frac{k_{endouptake}(1-A)F[mAb\cdot P\cdot P]_{late}}{V_{late}} - \frac{k_{endouptake}(1-A)(1-F)[mAb\cdot P\cdot P]_{late}}{V_{late}}$$

$$[mAb]'_{active} = -2k_{on,acidic}[mAb]_{active}[P]_{active} + k_{off,acidic}[mAb\cdot P]_{active} - \alpha k_{endouptake}(1-A)(1-F)[mAb]_{active} - \frac{\alpha k_{endouptake}(1-A)F[mAb]_{active}}{V_{active}}$$

$$[P]'_{active} = -2k_{on,acidic}[mAb]_{active}[P]_{active} + k_{off,acidic}[mAb\cdot P]_{active} - k_{on,acidic}[mAb\cdot P]_{active}[P]_{active} + 2k_{off,acidic}[mAb\cdot P\cdot P]_{active} - \alpha k_{endouptake}(1-A)[P]_{active}$$

$$[mAb\cdot P]'_{active} = k_{activeuptake}[mAb\cdot P]\frac{V}{V_{active}} + 2k_{on,acidic}[mAb]_{active}[P]_{active} -$$

-continued $$k_{off,acidic}[mAb\cdot P]_{active} - k_{on,acidic}[mAb\cdot P]_{active}[P]_{active} + 2k_{off,acidic}[mAb\cdot P\cdot P]_{active} - \alpha k_{endouptake}(1-A)[mAb\cdot P]_{active}$$

$$[mAb\cdot P\cdot P]'_{active} = 2k_{activeuptake}[mAb\cdot P\cdot P]\frac{V}{V_{active}} + k_{on,acidic}[mAb\cdot P]_{active}[P]_{active} - 2k_{off,acidic}[mAb\cdot P\cdot P]_{active} - \alpha k_{endouptake}(1-A)[mAb\cdot P\cdot P]_{active}$$

The parameters used in the model are described below in Table 3. In some cases, parameters are derived from other physiologically-relevant or measured quantities; these are indicated in the table as well.

TABLE 3

(N) = non-pH dependent mAb; (AS) = pH dependent mAb

| Parameter | Description | Value |
|---|---|---|
| $V$ | Blood volume | 2 mL |
| $V_{early}$ | Early endosome volume | 0.06 mL |
| $V_{late}$ | Late endosome volume | 0.06 mL |
| $V_{active}$ | Active uptake endosome volume | 0.3 mL |
| $k_{R,create}$ | Rate of LDLR synthesis | 0.1 nM/hr |
| $k_{P,create}$ | Rate of PCSK9 synthesis | 1.714 nM/hr |
| $k_{L,create}$ | Rate of LDL synthesis | 10.44 nM/hr |
| $k_{activeuptake}$ | First order rate of active PCSK9 uptake | $\ln(2)/t_{activeuptake}$ |
| $t_{activeuptake}$ | Time scale for active PCSK9 uptake | 1 hr |
| $k_{R,clear}$ | First order clearance rate for LDLR | 0.1872 $hr^{-1}$ |
| $k_{L,clear}$ | First order clearance rate for LDL | 0.018054 $hr^{-1}$ |
| $k_{protein,on}$ | Protein-protein association rate | 100000 $M^{-1} s^{-1}$ |
| $k_{L,off}$ | LDL/LDLR dissociation rate constant | $k_{protein,on} K_{d,L}$ |
| $K_{d,L}$ | LDL/LDLR affinity | 10 nM |
| $k_{P,off}$ | PCSK9/LDLR dissociation rate constant | $k_{protein,on} K_{d,P}$ |
| $K_{d,P}$ | PCSK9/LDLR affinity | 170 nM |
| $k_{internalize}$ | First order LDLR internalization rate | $\ln(2)/t_{internalize}$ |
| $t_{internalize}$ | Time scale for LDLR internalization | 5 min |
| $k_{recycle}$ | First order LDLR recycling rate | $\ln(2)/t_{recycle}$ |
| $t_{recycle}$ | Time scale for LDLR recycling | 10 min |
| $k_{on,neutral}$ | Antibody/PCSK9 association rate (pH 7.4) | $1.01 \times 10^5$ $M^{-1} s^{-1}$ (N) |
| | | $6.37 \times 10^4$ $M^{-1} s^{-1}$ (AS) |
| $k_{off,neutral}$ | Antibody/PCSK9 dissociation rate (pH 7.4) | $4.85 \times 10^{-4}$ $s^{-1}$ (N) |
| | | $5.16 \times 10^{-4}$ $s^{-1}$ (AS) |
| $k_{on,acidic}$ | Antibody/PCSK9 association rate (pH 5.5) | $3.73 \times 10^5$ $M^{-1} s^{-1}$ (N) |
| | | $1.6 \times 10^5$ $M^{-1} s^{-1}$ (AS) |
| $k_{off,acidic}$ | Antibody/PCSK9 dissociation rate (pH 5.5) | $1.94 \times 10^{-3}$ $s^{-1}$ (N) |
| | | 0.0187 $s^{-1}$ (AS) |
| $k_{endouptake}$ | Volume rate of uptake into early endosomes | 8 μL/min |
| A | Automatic recycling fraction | 0.7 (dimensionless) |
| F | FcRn-mediated antibody recycling efficiency | 0.972 (dimensionless) |
| α | Increase in active endosome processing time (compared to fluid phase endosomes) | 4 (dimensionless) |

Figure 1:
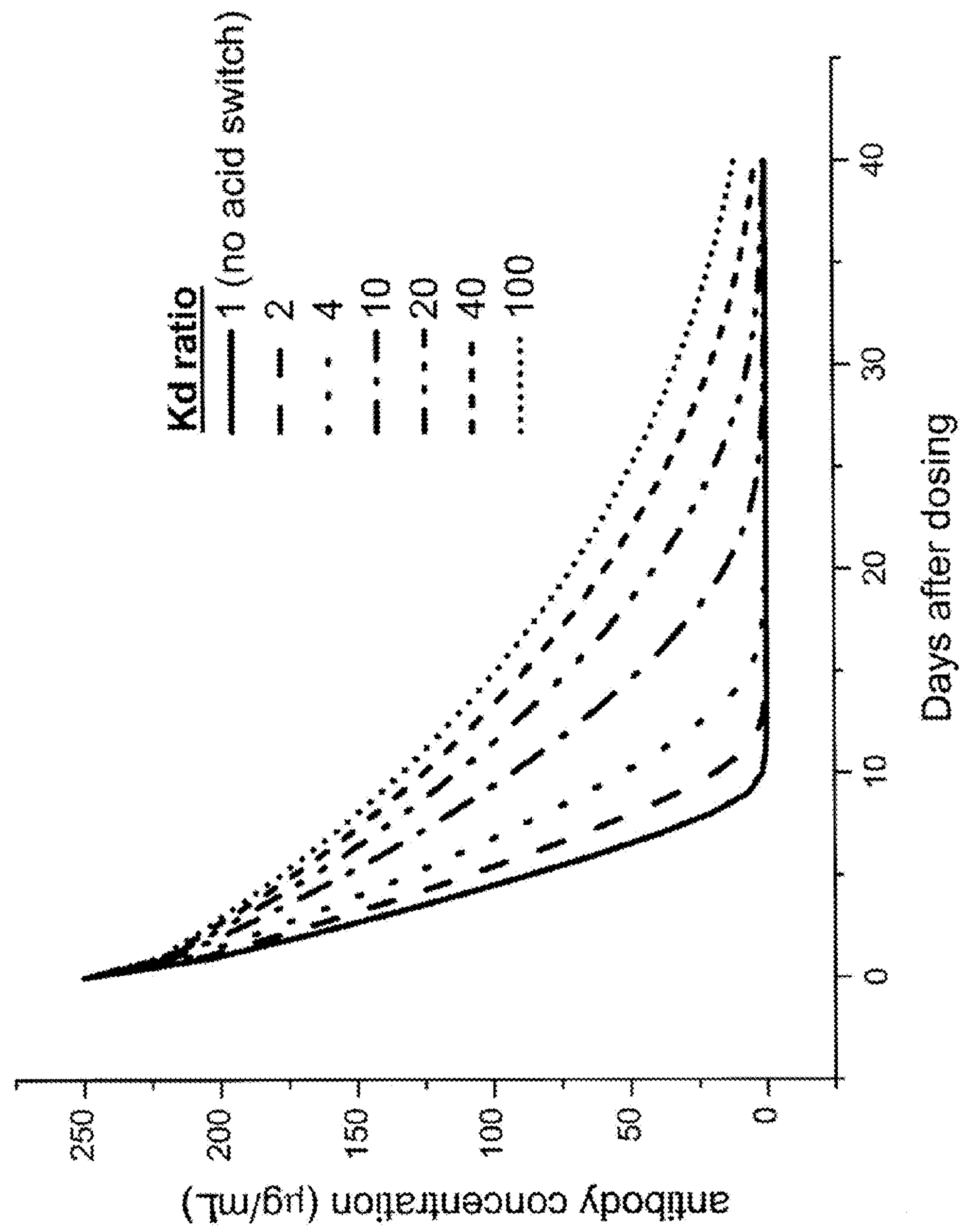
FIG. 1 is a graph showing the increase in antibody concentration over time as a function of the $K_D$ ratio.
Figure 2:
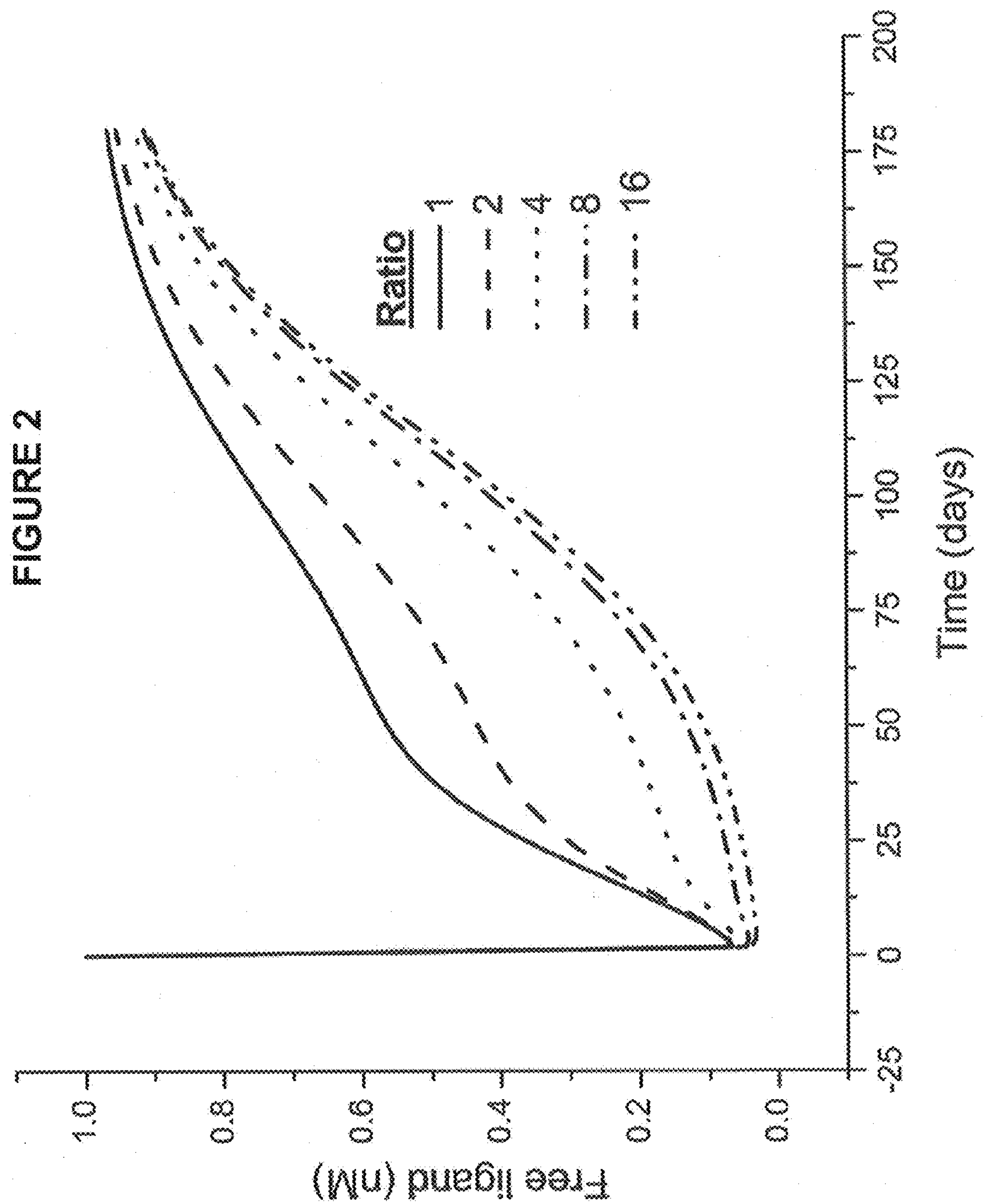
FIG. 2 is a graph showing the decrease in free ligand (antigen) over time as a function of the $K_D$ ratio.
Figure 3A:
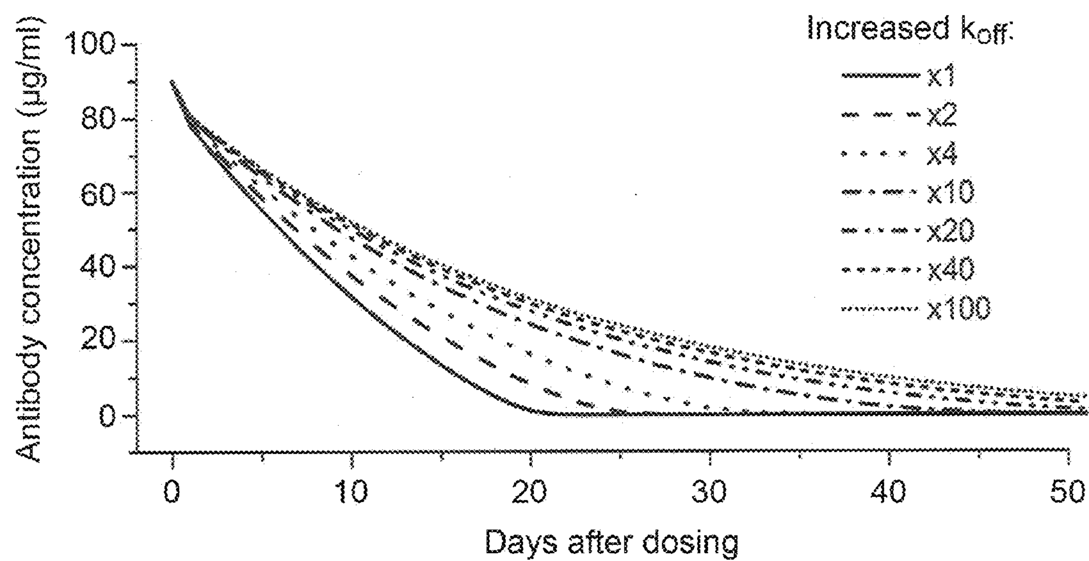
FIG. 3 is a graph showing the effect of changing $k_{off}$ and $k_{on}$ on antibody concentration over time.
Figure 3B:
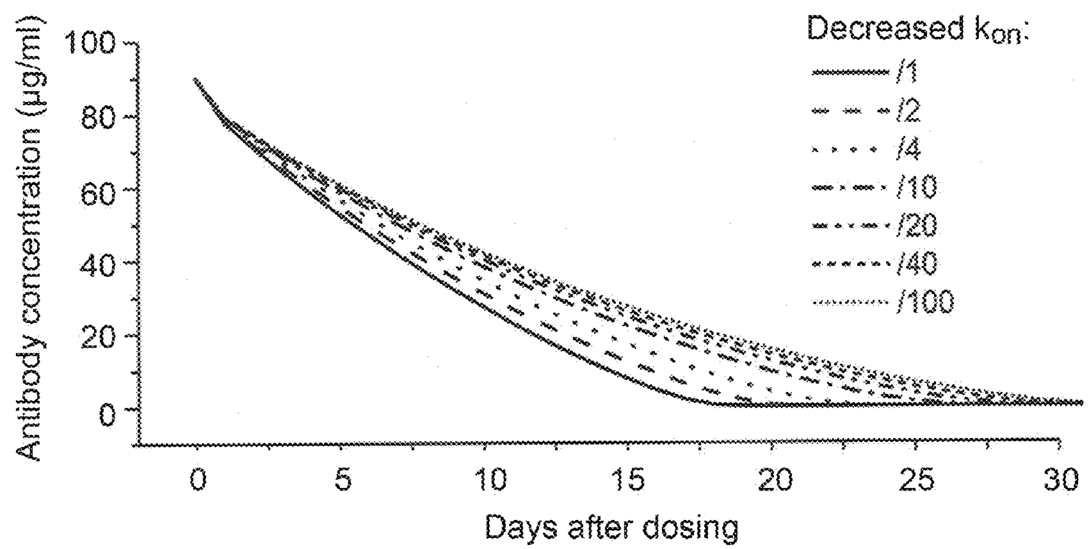

One depiction of the modeling is shown in FIG. 1. Increasing the $K_D$ ratio of endosomal pH (i.e., pH 5.5 or 6.0)/physiologic pH 7.4 from 1 to 2 resulted in an increase in antibody concentration over time, which was correlated with the value of the $K_D$ ratio. When the $K_D$ ratio was changed, or koff or kon, the antigen free ligand concentration was changed (FIG. 2) as well as antibody concentration (FIG. 3) in correlation with the increase $K_D$ ratio (FIG. 2), increased $k_{off}$ (FIG. 3A) and decreased $k_{on}$ (FIG. 3B). These results were not dependent upon designating whether endosomal pH was 5.5 or 6.0.

A heatmap display (FIG. 4) was constructed for a general model of antibodies with pH dependent binding, effectively showing how many days longer the antibody with pH dependent binding should decrease the serum concentration of antigen beyond that observed for a non-pH dependent antibody. Knockdown days are defined by integral of: $1-(C_{serum}(t)/(C_{serum}(t=0))$ from day 0 to day 100, e.g., a 100% reduction in serum concentration for N days followed by a return to pretreatment level would correspond to N knockdown days. The heat maps show the increase in knockdown days for the pH dependent antibodies, as compared to the control antibodies, based upon the $K_D$ at neutral pH and also the $K_D$ ratio (R). Effects are seen throughout all $K_D$ values modeled, particularly between 0.01 and 100 nM, and more particularly between $K_D$ of 0.1 and 10 nM. Changes in certain parameters, e.g., dose size, antibody kinetics, duration of simulation, or other quantities will lead to some differences in the values shown on the heat maps.

Modeling predictions for the performance of PCSK9 antibodies, with or without pH dependent binding, correlated well with actual experimental results. In FIG. 5A, the total antibody concentration over time after administering antibody 5A10, which has no pH dependent binding and a $K_D$ ratio of 1.1, is shown. Counterpart LDL levels are shown in FIG. 5B. In FIG. 6A, the total antibody concentration over time after administering antibody 5L1721H23_6L3H3, which has pH dependent binding and a $K_D$ ratio of 14.4, is shown. Counterpart LDL levels are also shown in FIG. 6B. For these models and experiments in FIGS. 5 and 6, a pH of 5.5 was assumed and the experimental $K_D$ values for the antibodies were calculated at pH 5.5. The pH dependent binding antibody demonstrated prolonged total antibody concentration and a prolonged inhibition of LDL levels as compared to 5A10. Further discussion of the general model for antibodies with pH dependent binding is shown in Example 4.

Example 2

Generating and Screening Anti-PCSK9 Antibodies with pH Dependent PCSK9 Binding Histidine scan mutagenesis was conducted for all CDRs of monoclonal antibody h5A10 (also known as 5A10 hu frame). This antibody originates from mouse monoclonal antibody 5A10 (also known as 5A10.B8), but has human framework regions. The sequence of the h5A10 antibody used as the starting template is shown below (CDRs are in bold font):

Variable Light chain:

(SEQ ID NO: 1)

DIQMTQSPSSLSASVGDRVTITCKASQDVSTAVAWYQQKPGKAPKLLIY

SASYRYTGVPSRFSGSGSGTDFTFTISSLQPEDIATYYCQQRYSTPRTF

GQGTKLEIK

Variable Heavy chain:

(SEQ ID NO: 2)

QVQLVQSGAEVKKPGASVKVSCKASGYTFTSYYMHWVRQAPGQGLEWMG

-continued

EINPSGGRTNYNEKFKSRVTMTRDTSTSTVYMELSSLRSEDTAVYYCAR

ERPLYAMDYWGQGTTVTVSS

The antibody h5A10 was cloned into a bacterial expression vector, which allows the expression of Fabs in the periplasm of *E. coli*. Using primers, every CDR position was mutated to histidine, resulting in 58 single histidine mutants of the h5A10 antibody.

Antibodies with these single histidine mutants were expressed in the periplasm of *E. coli* after induction with IPTG and purified using a histidine tag on the C-terminus of the CH1. The affinities of the purified Fabs were measured at pH 5.5 and 7.4 with Biacore. Mutations influencing the $K_D$ ratio of pH 5.5/pH 7.4 were found in four different CDR's (L1, L2, H2 & H3). The pH dependent change on the $K_D$ ranged between minimally decreased and significantly decreased.

Mutations from three CDRs (L1, L2 & H2) increased the $K_D$-ratio of pH 5.5/pH 7.4 without destroying the affinity at pH 7.4, and the antibodies combining the CDRs containing these mutations were generated. For h5A10 and all mutants, the heavy chain CDR1 (H1) sequence is GYTFTSYYMH (SEQ ID NO: 6). For 5A10, single, double, and triple mutants, and 5L1721H23_6H3, the light chain CDR3 (L3), is QQRYSTPRT (SEQ ID NO: 27). For the other affinity matured mutants and L1 L3-based mutants, L3 is QQRYSLWRT (SEQ ID NO: 12). The CDR sequences of the antibodies containing these various combinations of mutations are shown in Table 4 below. Sequence number identifiers are provided in parentheticals.

TABLE 4

| | L1 | L2 | H2 | H3 |
|---|---|---|---|---|
| h 5A10 | KASQDVSTAVA(13) | SASYRYT(17) | EINPSGGRTNYNEKFKS(19) | ERPLYAMDY(8) |
| Single mutants: | | | | |
| 5L-6 | KASQD**H**STAVA(14) | | | |
| 5L1-7 | KASQDV**H**TAVA(10) | | | |
| 5L2-1 | | **H**ASYRYT(11) | | |
| 5L2-4 | | SAS**H**RYT(18) | | |
| 5H2-3 | | | EI**H**PSGGRTNYNEKFKS(7) | |
| 5H3-5 | | | | ERPL**H**AMDY(21) |
| Double mutants: | | | | |
| 5L17 21 | KASQDV**H**TAVA(10) | **H**ASYRYT(11) | | |
| 5L17 24 | KASQDV**H**TAVA(10) | SAS**H**RYT(18) | | |
| 5L17H23 | KASQDV**H**TAVA(10) | | EI**H**PSGGRTNYNEKFKS(7) | |
| 5L21 24 | | **H**AS**H**RYT(19) | | |
| 5L21 H23 | | **H**ASYRYT(11) | EI**H**PSGGRTNYNEKFKS(7) | |
| 5L24 H23 | | SAS**H**RYT(18) | EI**H**PSGGRTNYNEKFKS(7) | |
| Triple mutants: | | | | |
| 5L17 21 H23 | KASQDV**H**TAVA(10) | **H**ASYRYT(11) | EI**H**PSGGRTNYNEKFKS(7) | |
| 5L17 24 H23 | KASQDV**H**TAVA(10) | SAS**H**RYT(18) | EI**H**PSGGRTNYNEKFKS(7) | |
| 5L1724H35 | KASQDV**H**TAVA(10) | SAS**H**RYT(18) | | ERPL**H**AMDY(21) |
| Affinity matured mutants: | | | | |
| 5L1721H23_6H3 | KASQDV**H**TAVA(10) | **H**ASYRYT(11) | EI**H**PSGGRTNYNEKFKS(7) | ERPLYA**SDL**(9) |
| 5L1721H23_6L3 | KASQDV**H**TAVA(10) | **H**ASYRYT(11) | EI**H**PSGGRTNYNEKFKS(7) | |
| 5L1724H23_6L3 | KASQDV**H**TAVA(10) | SAS**H**RYT(18) | EI**H**PSGGRTNYNEKFKS(7) | |
| 5L1721H23_6L3H3 | KASQDV**H**TAVA(10) | **H**ASYRYT(11) | EI**H**PSGGRTNYNEKFKS(7) | ERPLYA**SDL**(9) |
| 5L1724H23_6L3H3 | KASQDV**H**TAVA(10) | SAS**H**RYT(18) | EI**H**PSGGRTNYNEKFKS(7) | ERPLYA**SDL**(9) |
| L1L3-based mutants: | | | | |
| L1L3 | RASQGISSALA(15) | SASYRYT(17) | EISPFGGRTNYNEKFKS(20) | ERPLYA**SDL**(9) |
| 6L1721H23 | RASQGI**H**SALA(16) | **H**ASYRYT(11) | EI**H**PFGGRTNYNEKFKS(7) | |
| 6L1721 | RASQGI**H**SALA(16) | **H**ASYRYT(11) | | |
| 6L21H2335 | | **H**ASYRYT(11) | EI**H**PFGGRTNYNEKFKS(7) | |

No changes were made in the framework sequences for these antibodies as compared to 5A10.B8. For example, the sequences for the variable heavy chains of 5L1721H23_6L3 and 5L1721H23_6L3H3 are provided below. The same variable light chain was used in each of these antibodies and is also provided below. CDRs are highlighted in bold.

Variable light chain of 5L1721H23_6L3 and 5L1721H23_6L3H3:
(SEQ ID NO: 3)
DIQMTQSPSSLSASVGDRVTITCKASQDVHTAVAWYQQKPGKAPKLLIYHASYRYTGV

PSRFSGSGSGTDFTFTISSLQPEDIATYYCQQRYSLWRTFGQGTKLEIK

Variable heavy chain 5L1721H23_6L3:
(SEQ ID NO: 4)
QVQLVQSGAEVKKPGASVKVSCKASGYTFTSYYMHWVRQAPGQGLEWMGEIHPSGG

RTNYNEKFKSRVTMTRDTSTSTVYMELSSLRSEDTAVYYCARERPLYAMDY

WGQGTTVTVSS

Variable heavy chain 5L1721H23_6L3H3:
(SEQ ID NO: 5)
QVQLVQSGAEVKKPGASVKVSCKASGYTFTSYYMHWVRQAPGQGLEWMGEIHPSGG

RTNYNEKFKSRVTMTRDTSTSTVYMELSSLRSEDTAVYYCARERPLYASDL

WGQGTTVTVSS

Variable light chain (kappa) of 5L1721H23_6L3 and 5L1721H23_6L3H3
(SEQ ID NO: 23)
gatatccagatgacacagtccccatcctccctgtctgcctctgtgggcgaccgcgtcaccatcac ctgcaaggcctctcaggatgtgcatactgctgtagcctggtatcagcagaagccaggcaaagccc caaaactgctgatctaccatgcatcctaccgctacactggtgtcccatcacgcttcagtggcagt ggctctggtacagatttcaccttcaccattagcagcctgcaaccagaagatattgccacttatta ctgccagcaacgttatagtctgtggcgcacgttcggtcaaggcaccaagctggagatcaaa Variable heavy chain of 5L1721H236L3H3
(SEQ ID NO: 24)
caggtgcagctggtgcagtctggtgctgaggtgaagaagcctggcgcttccgtgaaggtttcctg caaagcatctggttacacctttaccagctactatatgcactgggtgcgccaagcccctggtcaag gcctggagtggatgggcgagattcatcctagcggcggtcgtactaactacaatgagaagttcaag agccgcgtgactatgactcgcgatacctccaccagcactgtctacatggaactgagctctctgcg ctctgaggacactgctgtgtattactgtgcccgcgagcgcccccctgtatgctagcgacctgtggg gccagggtaccacggtcaccgtctcctca These antibodies were expressed and purified for determination of their $K_D$ at 7.4 and their $K_D$ ratio of pH5.5/pH 7.4, as measured on a surface plasmon resonance Biacore 3000 biosensor equipped with a research-grade sensor chip using HBS-EP running buffer (Biacore AB, Uppsala, Sweden—now GE Healthcare). Rabbit polyclonal anti-Ms IgGs were amine-coupled at saturating levels onto the chip using a standard N-hydroxysuccinimide/ethyldimethylaminopropyl carbodiimide (NHS/EDC) chemistry. The buffer was switched to HBS-EP+1 mg/mL BSA+1 mg/mL CM-dextran. Full-length PCSK9 IgGs were diluted to about 15 μg/mL and captured for 1 min at 5 μL/min to give levels of about 500RU per flow cell, leaving one blank to serve as a reference channel. 3.73-302 nM hPCSK9 or 2.54-206 nM mPCSK9 were injected as a 5-membered 3-fold series for 1 min at 100 μL/min. Dissociation was monitored for 5 min. The chip was regenerated after the last injection of each titration with two 30 sec pulses of 100 mM phosphoric acid. Buffer cycles provided blanks for double-referencing the data, which were then fit globally to a simple binding model using Biaevaluation software v.4.1. Affinities were deduced from the quotient of the kinetic rate constants ($K_D=k_{off}/k_{on}$). The results for affinity to human PCSK9 are shown in Table 5, and the results for affinity to mouse PCSK9 are shown in Table 6. These data show that antibodies can be designed and selected to have higher affinity for human or mouse PCSK9 at pH 7.4, and a lower affinity at pH 5.5.

TABLE 5

Binding affinities for the anti-PCSK9 antibodies binding to human PCSK9 at pH 7.4 and 5.5.

| | huPCS K9 pH 7.4 | | | | huPCS K9 pH 5.5 | | | | pH |
|---|---|---|---|---|---|---|---|---|---|
| | kon (1/Ms) | Koff (1/s) | Rmax (RU) | KD (nM) | kon (1/Ms) | Koff (1/s) | Rmax (RU) | KD (nM) | 5.5/7.4 KD |
| 6L1721 | 3.29E+04 | 7.08E−05 | 880 | 2.2 | 1.66E+05 | 8.40E−04 | 1059 | 5.1 | 2.3 |
| 5A10.B8 | 4.38E+04 | 1.04E−04 | 1080 | 2.4 | 1.31E+05 | 3.91E−04 | 1020 | 3.0 | 1.3 |
| 5L1721H23__6L3H3 | 4.42E+04 | 1.72E−04 | 934 | 3.9 | 8.28E+04 | 4.80E−03 | 1430 | 58 | 14.9 |
| 6L1721H23 | 5.02E+04 | 2.01E−04 | 645 | 4.0 | 1.10E+05 | 2.61E−03 | 1140 | 24 | 6 |
| 5L1721H23__6L3 | 3.09E+04 | 2.14E−04 | 974 | 6.9 | 6.45E+04 | 0.0166 | 1320 | 257 | 37.2 |

TABLE 5-continued

Binding affinities for the anti-PCSK9 antibodies binding to human PCSK9 at pH 7.4 and 5.5.

| | huPCS K9 pH 7.4 | | | | huPCS K9 pH 5.5 | | | | pH |
|---|---|---|---|---|---|---|---|---|---|
| | kon (1/Ms) | Koff (1/s) | Rmax (RU) | KD (nM) | kon (1/Ms) | Koff (1/s) | Rmax (RU) | KD (nM) | 5.5/7.4 KD |
| 5L1721H23_6H3 | 3.74E+04 | 2.73E−04 | 461 | 7.3 | 1.41E+05 | 7.72E−03 | 398 | 55 | 7.5 |
| 5L1721H23 | 3.17E+04 | 3.99E−04 | 990 | 13 | 1.24E+05 | 0.0179 | 1030 | 144 | 11.1 |
| 5L1724H23_6L3H3 | 2.23E+04 | 3.42E−04 | 1020 | 15 | 9.55E+04 | 7.89E−03 | 1500 | 83 | 5.5 |
| 5L1724H23_6L3 | 3.59E+04 | 7.90E−04 | 910 | 22 | 7.54E+04 | 0.0407 | 1050 | 540 | 24.5 |
| 6L21H2335 | 5.81E+04 | 7.33E−03 | 892 | 126 | 6.55E+05 | 2.38E−01 | 624 | 363 | 2.9 |
| 5L1724H23 | — | — | 20 | — | 2.03E+05 | 7.93E−03 | 114 | 39 | |
| 5L1724H35 | — | — | 40 | — | — | — | 0 | — | |

TABLE 6

Binding affinities for the anti-PCSK9 antibodies binding to mouse PCSK9 at pH 7.4 and 5.5.

| | msPCK9 pH 7.4 | | | | msPCK9 pH 5.5 | | | | huPSCK9 |
|---|---|---|---|---|---|---|---|---|---|
| | kon (1/Ms) | Koff (1/s) | Rmax (RU) | KD (nM) | kon (1/Ms) | Koff (1/s) | Rmax (RU) | KD (nM) | pH 5.5/7.4 KD |
| 6L1721 | 8.80E+04 | 2.28E−04 | 1260 | 2.6 | 3.38E+05 | 1.77E−03 | 1120 | 5.2 | 2.0 |
| 5A10_WT | 1.01E+05 | 4.85E−04 | 1410 | 4.8 | 3.73E+05 | 1.94E−03 | 1050 | 5.2 | 1.1 |
| 5L1721H23_6L3H3 | 6.37E+04 | 5.16E−04 | 1630 | 8.1 | 1.60E+05 | 0.0187 | 1420 | 117 | 14.4 |
| 6L1721H23 | 6.48E+04 | 4.69E−04 | 1230 | 7.2 | 2.04E+05 | 7.29E−03 | 1220 | 36 | 5.0 |
| 5L1721H23_6L3 | 4.75E+04 | 6.76E−04 | 1600 | 14 | 1.05E+05 | 0.0428 | 1360 | 408 | 29.1 |
| 5L1721H23_6H3 | 1.13E+05 | 8.99E−04 | 615 | 8.0 | 3.07E+05 | 0.0341 | 460 | 111 | 13.9 |
| 5L1721H23 | 6.12E+04 | 1.41E−03 | 1380 | 23 | 1.02E+05 | 0.0588 | 1100 | 576 | 25.0 |
| 5L1724H23_6L3H3 | 6.31E+04 | 8.27E−04 | 1690 | 13 | 2.11E+05 | 0.0263 | 1520 | 125 | 9.6 |
| 5L1724H23_6L3 | 5.31E+04 | 2.18E−03 | 1440 | 41 | 1.60E+05 | 0.121 | 1100 | 756 | 18.4 |
| 6L21H2335 | 8.99E+04 | 1.72E−02 | 1340 | 191 | 5.26E+05 | 0.237 | 502 | 451 | 2.4 |
| 5L1724H23 | — | — | 40 | — | 2.73E+05 | 2.02E−02 | 91 | 74 | |
| 5L1724H35 | 4.43E+04 | 1.53E−03 | 164 | 35 | — | — | 0 | — | |

Affinity and kinetic parameters for PCSK9 antibodies h5A10 and 5L1721H23_6L3H3 as well as PCSK9 antibody H1M300N (see US2010/0166768, e.g., at Table 7). All experiments were performed on a Biacore 2000 biosensor.

An anti-human Fc sensor chip was prepared by activating all flow cells of a Biacore CM4 sensor chip with a 1:1 (v/v) mixture of 400 mM EDC and 100 mM NHS for 7 minutes, at a flow rate of 10 μL/min. An anti-human Fc reagent (Goat F(AB')2 Fragment to Human IgG Fc, Cappel Catalog #: 55053) was diluted to 60 μg/mL in 10 mM Sodium Acetate pH 5.0 and injected on all flow cells for 7 minutes at 20 μL/min. All flow cells were blocked with 100 mM ethylenediamine in 150 mM Borate buffer pH 8.5 for 7 minutes at 10 μL/min.

The kinetics assay was run using a kinetic titration methodology as described in Karlsson et al., Anal. Biochem 349, 136-147 (2006).

The same antibody (e.g., 5L1721H23_6L3H3) was captured onto downstream flow cells (flow cells 2, 3 and 4) at 2 μg/mL at a flow rate of 10 μL/min for 30 seconds, 60 seconds and 120 seconds for flow cells 2, 3 and 4 respectively. Flow cell 1 was used as a reference surface. Following capture of antibodies, PCSK9 was injected at 30 μL/min on all flow cells in a series of injections from low to high concentration. The top concentration was 200 nM PCSK9 and the dilution factor was 3-fold. Each PCSK9 injection was two-minutes, the dissociation time after the 200 nM PCSK9 injection was 20 minutes. A similar set of injections was performed with running buffer in place of PCSK9 for double-referencing purposes (double-referencing as described in Myszka, J. Mol. Recognit. 12, 279-284, 1999). After each analysis cycle all flow cells were regenerated with three 30-second injections of 75 mM Phosphoric Acid. The sensorgrams from flow cells 2 and 3 for a given PCSK9/antibody pair were fit globally to a simple 1:1 Langmuir with mass transport binding model.

The experiments were performed at pH 6.0 and 7.4 using sample and running buffers of 10 mM Sodium Phosphate, 150 mM Sodium Chloride, 0.05% Tween-20, pH 6 and 10 mM Sodium Phosphate, 150 mM Sodium Chloride, 0.05% Tween-20, pH 7.4, respectively.

TABLE 7 pH dependent binding

| | pH 6.0 (Sodium Phosphate) | | | | pH 7.4 (Sodium Phosphate) | | | | ratios | |
|---|---|---|---|---|---|---|---|---|---|---|
| Antibody | $k_a$ ($M^{-1}s^{-1}$) | $k_d$ ($s^{-1}$) | $t_{1/2}$ (min) | $K_D$ (pM) | $k_a$ ($M^{-1}s^{-1}$) | $k_d$ ($s^{-1}$) | $t_{1/2}$ (min) | $K_D$ (pM) | $K_D$, pH 6/$K_D$, pH 7.4 | $k_d$, pH 6/$k_d$, pH 7.4 |
| 5A10_WT | 3.31E+05 | <6E−5 | <193 | <181 | 2.41E+05 | <6E−05 | <193 | <249 | | |
| 5L1721H_236L3H3 | 3.07E+05 | 2.86E−03 | 4.0 | 9316 | 2.42E+05 | 1.74E−04 | 66.4 | 719 | 13.0 | 16.4 |
| H1M300N | 4.27E+05 | 3.21E−04 | 36.0 | 752 | 1.67E+05 | 6.92E−05 | 166.9 | 414 | 1.8 | 4.6 |

Example 3

PH Dependent PCSK9 Binding Antibodies have an Extended Pharmacodynamic Effect on Lowering Cholesterol A. pH Dependent PCSK9 Binding Antagonist Antibodies Lower Serum Cholesterol for an Extended Duration in Mice To determine if pH dependent PCSK9 binding antagonist antibodies can lower cholesterol levels in vivo for an extended duration as compared to non-pH dependent antibodies, the time course effects of acid sensitive antibodies 5L1721H23_6H3 and 5L1721H23_6L3H3 and non-acid sensitive antibodies h5A10 (only dosed at 10 mg/kg) and 5A10.B8 were tested on serum cholesterol when injected at 1, 3, or 10 mg/kg into mice. All four antibodies have similar binding affinities of 5-14 nM at neutral pH(PH 7.4) to mouse PCSK9. Antibodies 5L1721H23_6H3 and 5L1721H23_6L3H3 have reduced affinities of 117 nM and 408 nM, respectively, at pH 5.5, whereas h5A10 and 5A10.B8 have $K_D$ at pH 5.5 similar to that of 7.4 (5.2 nM). Male C57/bl6 mice, 6 to 7 weeks old, were kept on a 12 hr light/dark cycle, bled to collect approximately 70 μl serum on day −7. Antagonist PCSK9 antibodies and a control isotype matching monoclonal antibody that does not bind to any known mammalian proteins were injected IV into male 7 week old C57/bl6 mice and serum samples were collected on days 5, 12, 19, 26, 61, and 75 post-injection. All serum samples were analyzed for total cholesterol, triglyceride, HDL cholesterol on the Ace Alera instrument (Alfa Wassermann, West Caldwell, N.J.) and LDL cholesterol levels were calculated using Friedewald equation. FIG. 7 shows a rapid and dose-dependent decrease in total cholesterol levels following injection of a PCSK9 antagonist antibody. LDL cholesterol levels in mice were too low to be reliably measured and calculated. At 10 mg/kg dose, all four antibodies lowered HDL-cholesterol by 35-40% on days 5 and 12, while 5L1721H23_6H3 and 5L1721H23_6L3H3 injected animals did not recover until day 61, h5A10 and 5A10.B8 injected animals returned to baseline levels on days 26 and 33, respectively.

B. pH Dependent PCSK9 Binding Antibodies have an Extended Half-Life in Mice

Serum concentrations of antibody were determined in the same study described in example b to determine whether PH sensitive anti-PCSK9 antibodies resulted in extended antibody half-life. Normal anti-PCSK9 antibodies such as h5A10 and 5A10.B6 have dose-dependent shorter half life compared to antibodies that binds to other soluble antigens, due to PCSK9-mediated degradation of antibody/antigen complex. As shown in FIG. 8A, the pH dependent binding property reduced antibody degradation and extended the half life of anti-PCSK9 antibodies 5L1721H23_6H3 and 5L1721H23_6L3H3. To further demonstrate that the prolonged PK of 5L1721H23_6H3 and 5L1721H23_6L3H3 was a result of diminished PCSK9-mediated clearance of antibodies, a similar time course study was conducted in PCSK9 knockout mice. The differences in serum antibody concentrations and the rates of reduction between the PH sensitive and non-sensitive antibodies were insignificant until 3 mg/kg human PCSK9 was injected in the mice. Following this injection, the non-PH sensitive PCSK9 antibodies demonstrated increased degradation as compared to the PH sensitive antibodies and the negative control antibody (FIG. 8B). These results indicate that the observed decreased degradation of pH dependent PCSK9 binding PCSK9 antibodies results from dissociation of the antibody from PCSK9 and, therefore, rescue of the antibody from PCSK9-mediated degradation.

C. pH Sensitive PCSK9 Antagonist Antibodies Lower Serum Cholesterol for an Extended Duration in Monkeys FIG. 9B illustrates the effect of PH sensitive anti-PCSK9 antagonist antibodies 5L1721H23_6H3 and 5L1721H23_6L3H3 and non sensitive anti-PCSK9 antibody L1 L3 on serum LDL-cholesterol levels of cynomolgus as percent control. Antibodies (1.5 mg/kg of each) were administered on day 0 to female cynomolgus monkeys via i.v. bolus injection. The LDL-cholesterol was reduced to 50% of baseline by day in all three antibody-treated groups. While the LDL-cholesterol levels returned to baseline by day 10 following administration of non-pH sensitive antibody, LDL cholesterol stayed suppressed until day 21 in monkeys treated with pH sensitive antibodies. HDL levels remained essentially unchanged as a result of antibody treatment (FIG. 9A). FIG. 10 demonstrates that the half life of pH sensitive anti-PCSK9 antibodies were extended as compared to non-pH sensitive L1 L3.

Example 4

General Modeling for Antibodies with pH Dependent Antigen Binding

Computer modeling was used to predict whether an antibody with pH dependent binding to its generic antigen could impact antibody half life and/or the duration of lowering the antigen's amount or serum concentration. For purposes of this modeling, the following assumptions were made: 1) antibody, 1 uM dose of antibody in blood, 21 day antibody half-life; 2) simulation run for 100 days; antibody binding and pH dependent binding, $K_{on}$=1e5/M/s, $K_{off}$ @ neutral pH=$K_D$*$K_{on}$; pH dependent binding is modeled as an increase in $K_{off}$ in the acidic endosomes, $K_{off}$ at acidic pH=R*$K_{off}$ at neutral pH.

FIG. 15 details the trafficking model for antibodies with pH dependent binding used for modeling, and the equations defining the model are as follows:

*d/dt*(Normal_Dose)=−*k*_dist*Normal_Dose

*d/dt*(mAb)=*k*_dist*Normal_Dose−(mAb*kon*Normal_antigen)+(kon*KD*mAb_antigen)−*k*_blood_endo*mAb/$V_{Norm}$+*f*1*k_blood_endo*mAb_/$V_{Norm}$+(1−*f*1)**f*2**k*_blood_endo*mAb_*le*/$V_{Norm}$

*d/dt*(mAb_antigen)=(mAb*kon*Normal_antigen)−(kon*KD*mAb_antigen)−*k*_blood_endo*mAb_antigen/$V_{Norm}$+*f*1**k*_blood_endo*mAb_antigen_*e*/$V_{Norm}$+(1−*f*1)**f*2**k*_blood_endo*cmplx_*le*/$V_{Norm}$

*d/dt*(Normal_antigen)=−(mAb*kon*Normal_antigen)+(kon*KD*mAb_antigen)+ln(2)/antigen_halflife*antigen_level−ln(2)/antigen_halflife*Normal_antigen−*k*_blood_endo*Normal_antigen/$V_{Norm}$+*f*1**k*_blood_endo*Endosomes_antigen_*e*/$V_{Norm}$

*d/dt*(mAb_*e*)=*k*_blood_endo*mAb/$V_{Endo}$−*f*1**k*_blood_endo*mAb_*e*/$V_{Endo}$−(mAb_*e*kon*Endosomes*_antigen_*e*)+(kon*KD*mAb_antigen_*e*)−(1−*f*1)*k_blood_endo*mAb_*e*/$V_{Endo}$

*d/dt*(mAb_antigen_*e*)=*k*_blood_endo*mAb_antigen/$V_{Endo}$−*f*1**k*_blood_endo*mAb_antigen_*e*/$V_{Endo}$+(mAb_e*kon*Endosomes_antigen_*e*)−(kon*KD*mAb_antigen_*e*)−(1−*f*1)*k_blood_endo*mAb_antigen_*e*/$V_{Endo}$

*d/dt*(Endosomes_antigen_*e*)=*k*_blood_endo*Normal_antigen/$V_{Endo}$−*f*1**k*_blood_endo*Endosomes_antigen_*e*/$V_{Endo}$−(mAb_*e**kon*Endosomes_antigen_*e*)+

(kon*KD*mAb_antigen_e)−(1−f1)+ k_blood_endo*Endosomes_antigen_e/$V_{Endo}$ d/dt(mAb_le)=−(1−f1)*f2*k_blood_endo*mAb_le/ $V_{LEndo}$+(1−f1)*k_blood_endo*mAb_e/$V_{LEndo}$− (mAb_le*kon*Antigen_le)+(R*kon*KD*cplx_le)−(1−f1)*(1−f2)*k_blood_endo*mAb_le/ $V_{LEndo}$ d/dt(cplx_le)=−(1−f1)*f2*k_blood_endo*cplx_le/ $V_{Endo}$+(1−f1)*k_blood_endo*mAb_antigen_e/ $V_{LEndo}$+(mAb_le*kon*Antigen_le)− (R*kon*KD*cplx_le)−(1−f1)*(1−f2) *k_blood_endo*cplx_le/$V_{LEndo}$ d/dt(Antigen_le)=+(1−f1) *k_blood_endo_*Endosomes_antigen_e/ $V_{LEndo}$−(mAb_le*kon*Antigen_le)+ (R*kon*KD*cplx_le)−(1−f1) *k_blood_endo*Antigen_le/$V_{LEndo}$ The parameters used in the model are described below in Table 8.

TABLE 8

| | | |
|---|---|---|
| VNorm | 5.6 L | Volume of blood |
| VEndo | 0.06 L | Volume of early endosomes |
| VLEndo | 0.06 L | Volume of late endosomes |
| k_dist | 0.48/days | Rate of transport into blood |
| kon | 0.0001/nM/s | mAb-antigen association rate |
| k_blood_endo | 11.5 L/day | Rate of endosomal internalization |
| f1 | 0.7 | Fraction recycling from early endosomes |
| f2 | 0.95 | Fraction mAb recycling from late endosomes |
| $K_D$ | variable | Binding affinity [nM] |
| R | variable | Ratio of affinity at endosomal vs. neutral pH |
| antigen_halflife | variable | Half-life of antigen in blood [days] |
| antigen_level | variable | Level of antigen in the blood [nM] |

The heatmaps shown in FIG. 4 show how much more an antibody with pH dependent binding would impact antigen knockdown beyond knockdown by an antibody without pH dependent binding. This knockdown quantity is determined by measuring of the area between the free antigen curves for the two antibodies over the 100 day simulation. It can be thought of as how many days longer an antibody with pH dependent binding would impact antigen knockdown beyond knockdown by an antibody without pH dependent binding, though these two metrics do not have to correlate exactly. Lighter areas on the map reflect longer duration and/or stronger knockdown of free antigen. The heatmap for FIG. 11 shows how the potential antibodies with pH dependent antigen binding would impact antigen knockdown if the antigen was DKK1, IgE or C5. For each of these antigens, an antibody with pH dependent binding could extend antigen knockdown.

FIG. 12 shows more detailed modeling for an antibody with pH dependent binding to IgE. An extended duration of IgE knockdown occurs of the antibody has a $K_D$ of about 1 nM or greater and a $K_D$ ratio at pH 6.0/pH7.4 (R) of 3 or more.

Similar analysis for the antigen DKK1 is shown in FIG. 13 and for C5 in FIG. 14. For DKK1, an ideal range of $K_D$ is 1.0-100 nM across the $K_D$ ratio range of 3-30. For C5, the ideal range of $K_D$ is also 1.0-100 nM for the $K_D$ ratio range of 3-30.

Example 5

Generating and Screening Anti-IgE Antibodies with pH Dependent IgE Binding

Histidine substitutions were made at the positions of the underlined residues in anti-IgE antibody 5.948-H100Y, which has the following variable light chain (VL) and variable heavy chain (VH) amino acid sequences (CDRs are in bold font).

VL (SEQ ID NO: 25)

DIVMTQSPLSLPVTPGEPASISCRSSQSLLHRNGYNYLDWYLQK

PGQSPQLLIYLGSNRASGVPDRFSGSGSGTDFTLKISRVEAEDVGVYY

CMQALQTPPATFGGGTKVEIK

VH (SEQ ID NO: 26)

QVQLVQSGAEVKKPGASVKVSCKASGYTFTSYDINWVRQATGQG

LEWMGWMDPNSGNTGYAQKFQGRVTMTRNTSISTAYMELSSLRSEDTA

VYYCARGYYDSDGYYSFSGMDVWGQGTTVTVSS

The antibodies were tested for IgE binding at 25° C. For determination of affinities and kinetic constants, all experiments were performed on a Biacore T200 biosensor.

A biotin-capture surface was prepared by immobilization of NeutrAvidin: all flow cells of a Biacore CM4 sensor chip were activated with a 1:1 (v/v) mixture of 400 mM EDC and 100 mM NHS for 7 minutes, at a flow rate of 10 μL/min. NeutrAvidin (Pierce, product #: 31000) was diluted to 100 μg/mL in 10 mM Sodium Acetate pH 4.5 and injected on all flow cells for 7 minutes at 20 μL/min. All flow cells were blocked with 100 mM Ethylenediamine in 150 mM Borate buffer pH 8.5 for 7 minutes at 10 μL/min.

The IgE construct (human IgE-Fc (Ch2-Ch3-Ch4), expressed and purified in-house) was minimally biotinylated by incubating IgE with an equimolar amount of EZ-Link NHS-LC-LC-biotin (Thermo Scientific, catalog #21343) for 30 min at room temperature. Free biotin was removed via buffer exchange.

All Biacore experiments were performed using two of the four flow cells (1&2 or 3&4) of the sensor chip in parallel. The downstream flow cell was used as analysis flow cell while the other flow cell was used as a reference surface. Thus, biotinylated IgE (B-IgE) was captured on the analysis flow cell and every purified Fab fragment was injected over both. The sensorgram from the reference flow cell was subtracted from that of the analysis flow cell.

B-IgE was diluted into running buffer to a final concentration of 5 ug/mL immediately before capture. At pH 6.0, B-IgE was injected at 10 uL/min for 60 seconds. At pH 7.4, B-IgE was injected for 80 seconds to obtain similar capture levels. The kinetics assay was run using a kinetic titration methodology as described in Karlsson et al., Anal Biochem 349: 136-147, 2006.

Following capture of B-IgE, a purified Fab fragment was injected at 30 μL/min on analysis and reference flow cells in a series of injections from low to high concentration. The top concentration of Fab ranged from 30 nM to 200 nM and the dilution factor was 3-fold. Each Fab dilution was injected for 2 minutes, followed by a final dissociation time of 30 minutes after the last injection. A similar set of injections was performed with running buffer in place of Fab for double-referencing purposes (double-referencing as described in Myszka, J Mol Recognit 12: 279-284, 1999). The double-referenced sensorgrams were fit globally to a simple 1:1 Langmuir with mass transport binding model.

The experiments were performed at pH 6.0 and 7.4 using sample and running buffers of 10 mM Sodium Phosphate, 150 mM Sodium Chloride, 0.05% Tween-20, 1 mg/mL BSA, pH 6 and 10 mM Sodium Phosphate, 150 mM Sodium Chloride, 0.05% Tween-20, 1 mg/mL BSA, pH 7.4, respectively.

As shown in Table 9 below, histidine substitution in the IgE antibody 5.948-H100Y successfully resulted in antibodies with a faster $k_{off}$ at pH 6.0 and higher $K_D$ and $k_{off}$ ratios at pH 6.0/pH 7.4.

TABLE 9

| Effect of histidine substitution on antigen binding by IgE antibodies | | | | | | | | | | |
|---|---|---|---|---|---|---|---|---|---|---|
| | pH 6.0 | | | | pH 7.4 | | | | | KD ratio |
| | ka (M−1S−1) | kd (s−1) | kd (min) | KD (M) | ka (M−1S−1) | kd (s−1) | kd (min) | KD (M) | kd-pH6/ kd-pH7.4 | pH 6.0/pH 7.4 |
| H100Y | 1.02E+06 | 1.52E−04 | 76.00 | 1.49E−10 | 1.03E+06 | 5.01E−05 | 230.5879 | 4.87E−11 | 3.03 | 3.1 |
| L38H312H100Y | 3.29E+05 | 1.22E−02 | 0.95 | 3.71E−08 | 2.02E+05 | 1.08E−03 | 10.69672 | 5.33E−09 | 11.30 | 7.0 |
| H25H100Y | 2.98E+05 | 1.51E−03 | 7.65 | 5.08E−09 | 3.11E+05 | 1.97E−04 | 58.64189 | 6.34E−10 | 7.66 | 8.0 |
| H17H25H100Y | 2.23E+05 | 3.64E−03 | 3.17 | 1.63E−08 | 2.22E+05 | 4.22E−04 | 27.37548 | 1.90E−09 | 8.63 | 8.6 |

The disclosures of all references cited herein are hereby incorporated by reference herein.

It is claimed:

1. An isolated antibody which specifically binds to human PCSK9 and comprises a heavy chain variable region (VH) complementary determining region one (CDR1), a VH CDR2, and a VH CDR3 from the VH amino acid sequence shown in SEQ ID NO: 4 or 5, and further comprising the light chain variable region (VL) CDR1, CDR2, and CDR3 from the VL amino acid sequence shown in SEQ ID NO: 3.

2. The isolated antibody of claim 1, wherein the VH CDR1 has the amino acid sequence shown in SEQ ID NO: 6, the VH CDR2 has the amino acid sequence shown in SEQ ID NO: 7, the VH CDR3 has the amino acid sequence shown in SEQ ID NO: 9, the VL CDR1 has the amino acid sequence shown in SEQ ID NO: 10, the VL CDR2 has the amino acid sequence shown in SEQ ID NO: 11, and the VL CDR3 has the amino acid sequence shown in SEQ ID NO: 12.

3. The isolated antibody of claim 2, wherein the VH region comprises SEQ ID NO: 5 and the VL region comprises SEQ ID NO: 3.

4. An antibody or antigen-binding portion thereof which specifically binds to human PCSK9, encoded by the plasmid deposited at the ATCC and having ATCC Accession No. PTA-10547, or PTA-10548, and/or PTA-10549.

* * * * *

SEQUENCE LISTING

```
<160> NUMBER OF SEQ ID NOS: 27

<210> SEQ ID NO 1
<211> LENGTH: 107
<212> TYPE: PRT
<213> ORGANISM: Homo sapien

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Thr Pro Arg
                85                  90                  95

Thr Phe Gly Gln Gly Thr Lys Leu Glu Ile Lys
            100                 105


<210> SEQ ID NO 2
<211> LENGTH: 118
<212> TYPE: PRT
<213> ORGANISM: Homo sapien

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Asn Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
            100                 105                 110
```

```
Thr Val Thr Val Ser Ser
        115


<210> SEQ ID NO 3
<211> LENGTH: 107
<212> TYPE: PRT
<213> ORGANISM: Homo sapien

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105


<210> SEQ ID NO 4
<211> LENGTH: 118
<212> TYPE: PRT
<213> ORGANISM: Homo sapien

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
            100                 105                 110

Thr Val Thr Val Ser Ser
        115


<210> SEQ ID NO 5
<211> LENGTH: 118
<212> TYPE: PRT
<213> ORGANISM: Homo sapien

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115


<210> SEQ ID NO 6
<211> LENGTH: 10
<212> TYPE: PRT
<213> ORGANISM: Homo sapien

<400> SEQUENCE: 6

Gly Tyr Thr Phe Thr Ser Tyr Tyr Met His
1               5                   10


<210> SEQ ID NO 7
<211> LENGTH: 17
<212> TYPE: PRT
<213> ORGANISM: Homo sapien

<400> SEQUENCE: 7

Glu Ile His Pro Ser Gly Gly Arg Thr Asn Tyr Asn Glu Lys Phe Lys
1               5                   10                  15

Ser


<210> SEQ ID NO 8
<211> LENGTH: 9
<212> TYPE: PRT
<213> ORGANISM: Homo sapien

<400> SEQUENCE: 8

Glu Arg Pro Leu Tyr Ala Met Asp Tyr
1               5


<210> SEQ ID NO 9
<211> LENGTH: 9
<212> TYPE: PRT
<213> ORGANISM: Homo sapien

<400> SEQUENCE: 9

Glu Arg Pro Leu Tyr Ala Ser Asp Leu
1               5


<210> SEQ ID NO 10
<211> LENGTH: 11
<212> TYPE: PRT
<213> ORGANISM: Homo sapien

<400> SEQUENCE: 10

Lys Ala Ser Gln Asp Val His Thr Ala Val Ala
1               5                   10


<210> SEQ ID NO 11
<211> LENGTH: 7
<212> TYPE: PRT
```

<213> ORGANISM: Homo sapien

<400> SEQUENCE: 11

His Ala Ser Tyr Arg Tyr Thr
1 5

<210> SEQ ID NO 12
<211> LENGTH: 9
<212> TYPE: PRT
<213> ORGANISM: Homo sapien

<400> SEQUENCE: 12

Gln Gln Arg Tyr Ser Leu Trp Arg Thr
1 5

<210> SEQ ID NO 13
<211> LENGTH: 11
<212> TYPE: PRT
<213> ORGANISM: Homo sapien

<400> SEQUENCE: 13

Lys Ala Ser Gln Asp Val Ser Thr Ala Val Ala
1 5 10

<210> SEQ ID NO 14
<211> LENGTH: 11
<212> TYPE: PRT
<213> ORGANISM: Homo sapien

<400> SEQUENCE: 14

Lys Ala Ser Gln Asp His Ser Thr Ala Val Ala
1 5 10

<210> SEQ ID NO 15
<211> LENGTH: 11
<212> TYPE: PRT
<213> ORGANISM: Homo sapien

<400> SEQUENCE: 15

Arg Ala Ser Gln Gly Ile Ser Ser Ala Leu Ala
1 5 10

<210> SEQ ID NO 16
<211> LENGTH: 11
<212> TYPE: PRT
<213> ORGANISM: Homo sapien

<400> SEQUENCE: 16

Arg Ala Ser Gln Gly Ile His Ser Ala Leu Ala
1 5 10

<210> SEQ ID NO 17
<211> LENGTH: 7
<212> TYPE: PRT
<213> ORGANISM: Homo sapien

<400> SEQUENCE: 17

Ser Ala Ser Tyr Arg Tyr Thr
1 5

<210> SEQ ID NO 18
<211> LENGTH: 7
<212> TYPE: PRT
<213> ORGANISM: Homo sapien

<400> SEQUENCE: 18

Ser Ala Ser His Arg Tyr Thr
1 5

<210> SEQ ID NO 19
<211> LENGTH: 17
<212> TYPE: PRT
<213> ORGANISM: Homo sapien

<400> SEQUENCE: 19

Glu Ile Asn Pro Ser Gly Gly Arg Thr Asn Tyr Asn Glu Lys Phe Lys
1 5 10 15

Ser

<210> SEQ ID NO 20
<211> LENGTH: 17
<212> TYPE: PRT
<213> ORGANISM: Homo sapien

<400> SEQUENCE: 20

Glu Ile Ser Pro Phe Gly Gly Arg Thr Asn Tyr Asn Glu Lys Phe Lys
1 5 10 15

Ser

<210> SEQ ID NO 21
<211> LENGTH: 9
<212> TYPE: PRT
<213> ORGANISM: Homo sapien

<400> SEQUENCE: 21

Glu Arg Pro Leu His Ala Met Asp Tyr
1 5

<210> SEQ ID NO 22
<211> LENGTH: 15
<212> TYPE: PRT
<213> ORGANISM: Homo sapien

<400> SEQUENCE: 22

Gly Gly Gly Gly Ser Gly Gly Gly Gly Ser Gly Gly Gly Gly Ser
1 5 10 15

<210> SEQ ID NO 23
<211> LENGTH: 321
<212> TYPE: DNA
<213> ORGANISM: Homo sapien

<400> SEQUENCE: 23
gatatccaga tgacacagtc cccatcctcc ctgtctgcct ctgtgggcga ccgcgtcacc 60
atcacctgca aggcctctca ggatgtgcat actgctgtag cctggtatca gcagaagcca 120
ggcaaagccc caaaactgct gatctaccat gcatcctacc gctacactgg tgtcccatca 180
cgcttcagtg gcagtggctc tggtacagat ttcaccttca ccattagcag cctgcaacca 240
gaagatattg ccacttatta ctgccagcaa cgttatagtc tgtggcgcac gttcggtcaa 300
ggcaccaagc tggagatcaa a 321

<210> SEQ ID NO 24
<211> LENGTH: 354
<212> TYPE: DNA
<213> ORGANISM: Homo sapien

<400> SEQUENCE: 24

```
caggtgcagc tggtgcagtc tggtgctgag gtgaagaagc ctggcgcttc cgtgaaggtt      60

tcctgcaaag catctggtta cacctttacc agctactata tgcactgggt gcgccaagcc     120

cctggtcaag gcctggagtg gatgggcgag attcatccta gcggcggtcg tactaactac     180

aatgagaagt tcaagagccg cgtgactatg actcgcgata cctccaccag cactgtctac     240

atggaactga gctctctgcg ctctgaggac actgctgtgt attactgtgc ccgcgagcgc     300

cccctgtatg ctagcgacct gtggggccag ggtaccacgg tcaccgtctc ctca           354
```

<210> SEQ ID NO 25
<211> LENGTH: 113
<212> TYPE: PRT
<213> ORGANISM: Homo sapien

<400> SEQUENCE: 25

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Ala Thr Phe Gly Gly Gly Thr Lys Val Glu Ile
            100                 105                 110

Lys
```

<210> SEQ ID NO 26
<211> LENGTH: 125
<212> TYPE: PRT
<213> ORGANISM: Homo sapien

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Asp Ser Asp Gly Tyr Tyr Ser Phe Ser Gly Met
            100                 105                 110

Asp Val Trp Gly Gln Gly Thr Thr Val Thr Val Ser Ser
        115                 120                 125
```

<210> SEQ ID NO 27

-continued

```
<211> LENGTH: 9
<212> TYPE: PRT
<213> ORGANISM: Homo sapien

<400> SEQUENCE: 27

Gln Gln Arg Tyr Ser Thr Pro Arg Thr
1               5
```